US008765919B2

(12) United States Patent
Kaye

(10) Patent No.: US 8,765,919 B2
(45) Date of Patent: Jul. 1, 2014

(54) TOX3 AS A BIOMARKER FOR BREAST CANCER

(75) Inventor: Jonathan Kaye, San Diego, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/488,058

(22) Filed: Jun. 4, 2012

(65) Prior Publication Data

US 2012/0304319 A1 Nov. 29, 2012

Related U.S. Application Data

(63) Continuation-in-part of application No. PCT/US2010/058795, filed on Dec. 2, 2010.

(60) Provisional application No. 61/266,918, filed on Dec. 4, 2009.

(51) Int. Cl.
*C07K 16/32* (2006.01)
*A61K 39/395* (2006.01)

(52) U.S. Cl.
USPC ................ 530/388.8; 530/388.85; 424/155.1; 424/156.1

(58) Field of Classification Search
CPC ............. A61K 39/39558; C07K 16/30; C07K 16/3015; C07K 16/32; C07K 2317/20; C07K 2317/24; G01N 33/57415
See application file for complete search history.

(56) References Cited

U.S. PATENT DOCUMENTS 7,745,391 B2 * 6/2010 Mintz et al. .................. 514/19.3
2004/0053245 A1 * 3/2004 Tang et al. ......................... 435/6
2008/0292546 A1 11/2008 Clarke et al.
2009/0175844 A1 7/2009 Nakamura et al.
2010/0120788 A1 * 5/2010 Wang et al. .............. 514/252.19
2013/0225430 A1 8/2013 Kaye et al.

FOREIGN PATENT DOCUMENTS

WO 2011069014 A1 6/2011

OTHER PUBLICATIONS

Ripperger et al., Eur J Human Genetics 2009; 17:722-31.*
Yuan et al., Proc Nat'l Acad Sci 106(8):2909-14 (Feb. 24, 2009).*
O'Flaherty and Kaye, BMC Genomics, 2003; 4:13, pp. 1-10.*
Campbell AM, in Monoclonal Antibody Technology, Elsevier Science Publishers B.V., The Netherlands, 1984, Chapter 1, pp. 1-32.*
Rossi et al. Am. J. Clin. Pathol. 2005; 124:295-302.*
PCT/US2010/058795 International Preliminary Report on Patentability dated Jun. 5, 2012.
PCT/US2010/058795 Written Opinion dated Apr. 25, 2011.
PCT/US2010/058795 International Search Report dated Apr. 25, 2011.
Nordgard et al. Genes Harbouring Susceptibility SNPs are Differentially Expressed in the Breast Cancer Subtypes. Breast Cancer Research (2007). 9(113):1-2.
U.S. Appl. No. 13/761,029 Restriction Requirement dated Sep. 23, 2013.

* cited by examiner

*Primary Examiner* — Sheela J Huff
*Assistant Examiner* — Jessica H Roark
(74) *Attorney, Agent, or Firm* — Seth D. Levy; Nixon Peabody LLP

(57) ABSTRACT

The invention provides compositions and methods for detecting and/or modulating TOX3 gene expression and/or biological activity. Such compositions and methods find utility in the detection and/or treatment of certain subsets of cancers, e.g. breast cancer. In particular, the inventive compositions and methods are drawn to production and use of anti-TOX3 antibodies and TOX3 nucleic acids for both detection and modulation of TOX3. The invention also provides for pharmaceutical compositions and methods for the modulation of TOX3 in a subject in need thereof. Further aspects of the invention relate to transgenic mice that either over-express or inducibly express TOX3.

4 Claims, 8 Drawing Sheets

A

B

A
var1 MDVRFYPAAAGDPASLDFAQCLGYYGYSKFGNNNNYM. SEQ ID NO: 1
var2 MKCQPRSGARRIEERLHYLITTYLKFGNNNNYM. SEQ ID NO: 5

B

SEQ ID NO: 6
SEQ ID NO: 4

C

D

E

D

E

A

B

SEQUENCE LISTING

<160> NUMBER OF SEQ ID NOS: 7

<210> SEQ ID NO 1
<211> LENGTH: 589
<212> TYPE: PRT
<213> ORGANISM: Homo sapiens

<400> SEQUENCE: 1

Met Asp Val Arg Phe Tyr Pro Ala Ala Ala Gly Asp Pro Ala Ser Leu
1 5 10 15

Asp Phe Ala Gln Cys Leu Gly Tyr Tyr Gly Tyr Ser Lys Phe Gly Asn
20 25 30

Asn Asn Asn Tyr Met Asn Met Ala Glu Ala Asn Asn Ala Phe Phe Ala
35 40 45

Ala Ser Glu Gln Thr Phe His Thr Pro Ser Leu Gly Asp Glu Glu Phe
50 55 60

Glu Ile Pro Pro Ile Thr Pro Pro Pro Glu Ser Asp Pro Ala Leu Gly
65 70 75 80

Met Pro Asp Val Leu Leu Pro Phe Gln Ala Leu Ser Asp Pro Leu Pro
85 90 95

Ser Gln Gly Ser Glu Phe Thr Pro Gln Phe Pro Pro Gln Ser Leu Asp
100 105 110

Leu Pro Ser Ile Thr Ile Ser Arg Asn Leu Val Glu Gln Asp Gly Val
115 120 125

Leu His Ser Ser Gly Leu His Met Asp Gln Ser His Thr Gln Val Ser
130 135 140

Gln Tyr Arg Gln Asp Pro Ser Leu Ile Met Arg Ser Ile Val His Met
145 150 155 160

Thr Asp Ala Ala Arg Ser Gly Val Met Pro Pro Ala Gln Leu Thr Thr
165 170 175

Ile Asn Gln Ser Gln Leu Ser Ala Gln Leu Gly Leu Asn Leu Gly Gly
180 185 190

Ala Ser Met Pro His Thr Ser Pro Ser Pro Pro Ala Ser Lys Ser Ala
195 200 205

Thr Pro Ser Pro Ser Ser Ser Ile Asn Glu Glu Asp Ala Asp Glu Ala
210 215 220

Asn Arg Ala Ile Gly Glu Lys Arg Ala Ala Pro Asp Ser Gly Lys Lys
225 230 235 240

Pro Lys Thr Pro Lys Lys Lys Lys Lys Lys Asp Pro Asn Glu Pro Gln
245 250 255

Lys Pro Val Ser Ala Tyr Ala Leu Phe Phe Arg Asp Thr Gln Ala Ala
260 265 270

Ile Lys Gly Gln Asn Pro Asn Ala Thr Phe Gly Glu Val Ser Lys Ile
275 280 285

Val Ala Ser Met Trp Asp Ser Leu Gly Glu Glu Gln Lys Gln Val Tyr
290 295 300

Lys Arg Lys Thr Glu Ala Ala Lys Lys Glu Tyr Leu Lys Ala Leu Ala
305 310 315 320

Ala Tyr Arg Ala Ser Leu Val Ser Lys Ala Ala Ala Glu Ser Ala Glu
325 330 335

Ala Gln Thr Ile Arg Ser Val Gln Gln Thr Leu Ala Ser Thr Asn Leu
340 345 350

Thr Ser Ser Leu Leu Leu Asn Thr Pro Leu Ser Gln His Gly Thr Val
355 360 365

```
Ser Ala Ser Pro Gln Thr Leu Gln Gln Ser Leu Pro Arg Ser Ile Ala
    370                 375                 380

Pro Lys Pro Leu Thr Met Arg Leu Pro Met Asn Gln Ile Val Thr Ser
385                 390                 395                 400

Val Thr Ile Ala Ala Asn Met Pro Ser Asn Ile Gly Ala Pro Leu Ile
                405                 410                 415

Ser Ser Met Gly Thr Thr Met Val Gly Ser Ala Pro Ser Thr Gln Val
            420                 425                 430

Ser Pro Ser Val Gln Thr Gln Gln His Gln Met Gln Leu Gln Gln Gln
        435                 440                 445

Gln Gln Gln Gln Gln Gln Gln Met Gln Gln Met Gln Gln Gln Gln Leu
    450                 455                 460

Gln Gln His Gln Met His Gln Gln Ile Gln Gln Gln Met Gln Gln Gln
465                 470                 475                 480

His Phe Gln His His Met Gln Gln His Leu Gln Gln Gln Gln Gln His
                485                 490                 495

Leu Gln Gln Gln Ile Asn Gln Gln Gln Leu Gln Gln Gln Leu Gln Gln
            500                 505                 510

Arg Leu Gln Leu Gln Gln Leu Gln His Met Gln His Gln Ser Gln Pro
        515                 520                 525

Ser Pro Arg Gln His Ser Pro Val Ala Ser Gln Ile Thr Ser Pro Ile
    530                 535                 540

Pro Ala Ile Gly Ser Pro Gln Pro Ala Ser Gln Gln His Gln Ser Gln
545                 550                 555                 560

Ile Gln Ser Gln Thr Gln Thr Gln Val Leu Ser Gln Ala Ile Pro Thr
                565                 570                 575

Ile Cys Glu Ser Asn Cys Leu Met Asn Pro Gly Thr Tyr
            580                 585


<210> SEQ ID NO 2
<211> LENGTH: 238
<212> TYPE: PRT
<213> ORGANISM: Homo sapiens

<400> SEQUENCE: 2

Met Asp Val Arg Phe Tyr Pro Ala Ala Ala Gly Asp Pro Ala Ser Leu
1               5                   10                  15

Asp Phe Ala Gln Cys Leu Gly Tyr Tyr Gly Tyr Ser Lys Phe Gly Asn
            20                  25                  30

Asn Asn Asn Tyr Met Asn Met Ala Glu Ala Asn Asn Ala Phe Phe Ala
        35                  40                  45

Ala Ser Glu Gln Thr Phe His Thr Pro Ser Leu Gly Asp Glu Glu Phe
    50                  55                  60

Glu Ile Pro Pro Ile Thr Pro Pro Pro Glu Ser Asp Pro Ala Leu Gly
65                  70                  75                  80

Met Pro Asp Val Leu Leu Pro Phe Gln Ala Leu Ser Asp Pro Leu Pro
                85                  90                  95

Ser Gln Gly Ser Glu Phe Thr Pro Gln Phe Pro Pro Gln Ser Leu Asp
            100                 105                 110

Leu Pro Ser Ile Thr Ile Ser Arg Asn Leu Val Glu Gln Asp Gly Val
        115                 120                 125

Leu His Ser Ser Gly Leu His Met Asp Gln Ser His Thr Gln Val Ser
    130                 135                 140

Gln Tyr Arg Gln Asp Pro Ser Leu Ile Met Arg Ser Ile Val His Met
145                 150                 155                 160
```

-continued

```
Thr Asp Ala Ala Arg Ser Gly Val Met Pro Pro Ala Gln Leu Thr Thr
                165                 170                 175

Ile Asn Gln Ser Gln Leu Ser Ala Gln Leu Gly Leu Asn Leu Gly Gly
            180                 185                 190

Ala Ser Met Pro His Thr Ser Pro Ser Pro Pro Ala Ser Lys Ser Ala
        195                 200                 205

Thr Pro Ser Pro Ser Ser Ser Ile Asn Glu Glu Asp Ala Asp Glu Ala
    210                 215                 220

Asn Arg Ala Ile Gly Glu Lys Arg Ala Ala Pro Asp Ser Gly
225                 230                 235


<210> SEQ ID NO 3
<211> LENGTH: 1734
<212> TYPE: DNA
<213> ORGANISM: Rattus norvegicus

<400> SEQUENCE: 3

atggatgtga ggttctaccc cgcggcggcc ggggatcccg ccggcctgga cttcgcgcag     60

tgcctggggt actacggcta cagcaagttg ggaaataata actacatgaa catggctgag    120

gcaaacaacg ccttctttgc tgccagtgag cagacattcc acacgccaag ccttggggat    180

gaagagtttg aaattccgcc gatcacgcct cctccagagt cagaccccac cctgggcatg    240

cccgatgtac tgctaccctt tcagacactc agcgatccgt tgccttccca gggaaatgag    300

ttcacacccc agtttccccc tcagagcctg gatcttcctt ccatcacaat ctcaaggaat    360

ctggtggagc aagatggtgt gcttcatagc aacgggctgc atatggatca gagccacaca    420

caagtgtcgc agtaccgcca ggatccttct ttggtcatga ggtcaattgt ccacatgaca    480

gatgctgctc gctctgggat catgcctcct gcccaactga ccaccatcaa ccagtctcag    540

ctcagtgcac agttgggctt gaatctggga ggagccagtg tgccccacac gtctccttca    600

cctccagcaa gcaaatcagc cactccctcc ccttccagct ctatcaatga agaggatgct    660

gatgaaacaa acagagccgt tggagagaaa agaacagccc cagattctgg caagaagccc    720

aagactccaa agaaaaagaa aaagaaagat cccaacgagc ctcagaagcc agtgtcagca    780

tacgccctgt ttttcagaga tacacaggct gcaattaaag gtcaaaaccc caatgcgacc    840

tttggagaag tctcaaaaat tgtagcatct atgtgggaca gccttggaga ggagcaaaag    900

caggtatata aaaggaaaac agaagctgcc aagaaagaat atttgaaggc cctggctgcc    960

taccgggcca gcctcgtttc taaggctgct gctgagtccg cagaagccca gactatccgc   1020

tctgtccagc agactctggc atcaaccaac ctgacatcct ctctccttct gaacacgtca   1080

ctgtctcaac atgggacagt cccggcttca cctcagactc tcccgcagtc actccctagg   1140

tcgattgccc ccaaaccctt aaccatgaga ctacccatga gccagattgt cacatcagtc   1200

accattgcag ccaacatgcc ctcgaacatt ggggctccac ttatcagctc catgggaacg   1260

accatggttg gctcagtatc ctccacgcag gtgagccctt cggtacaaac ccagcaacat   1320

cagctgcagc tgcagcagca gcaacaacag cagcagcagc agatgcagca gatgcaacat   1380

cagcagctgc agcagcacca gatgcatcag cagattcagc agcagatgca gcagcagcat   1440

ttccagcacc acatgcaaca gcacctgcag cagcagcaac agcagcacct ccagcagcag   1500

atcagccaac agcagctgca gcagcagctg cagcagcatc tccagctgca gcagcagctg   1560

cagcacatgc agcaccagtc tcagccttct ccccggcagc actcgcccgt cacctcacag   1620

atcacgtccc ccatccccgc cattggcagc ccccagccag cctctcagca gcaccagcct   1680
```

-continued

```
caaatccagt cgcagacaca gactcaagtg ttaccgcagg tcagtatttt ttaa        1734


<210> SEQ ID NO 4
<211> LENGTH: 2849
<212> TYPE: DNA
<213> ORGANISM: Homo sapiens

<400> SEQUENCE: 4

gcggccgcgg ctcccgagct cctcgggctc tgggtcccgg cgcccctccg gccgcgagtc     60

ccacgcgcca cccccgggcg ccctcgacgg tggatctagc ggcggcgagg aggcgggtcc    120

cggccccggc gaaccccagt cccggccccc ggcccccggc ccagcttcgg catggatgtg    180

aggttctacc ccgcggcggc cggggaccct gccagcctgg acttcgcgca gtgcctgggg    240

tactacggct acagcaagtt tggaaataat aataactata tgaatatggc tgaggcgaac    300

aatgcgttct tcgctgccag tgagcagaca ttccacacac caagccttgg ggacgaggaa    360

ttcgaaattc caccaatcac gcctcctcca gagtcagacc ctgccctagg catgccggat    420

gtactgctac cctttcaagc cctcagcgat ccattgcctt cccagggaag tgaattcaca    480

ccccagtttc cccctcaaag cctggacctc ccttccatta caatctcaag aaatctcgtg    540

gaacaagatg gcgtgcttca tagcagtggg ttgcatatgg atcagagcca cacacaagtg    600

tcccagtacc ggcaggatcc ctccctgatc atgcggtcca tcgtccacat gaccgatgct    660

gcgcgttctg ggtcatgcc tcctgcccag ctcaccacca tcaaccagtc tcagctcagc    720

gcccagttgg ggttgaattt gggaggtgcc agtatgcctc acacatctcc ttcacctcca    780

gcaagcaaat cagccactcc ctccccttcc agctccatca atgaagagga tgctgatgaa    840

gccaacagag ccattggaga gaaaagagct gctccagact ctggcaagaa gcccaagact    900

ccaaagaaaa agaaaaagaa agatcccaat gagccacaga agccagtgtc agcatatgcc    960

ctgtttttca gagacacaca ggctgcaatt aaaggtcaaa accccaatgc aacctttgga   1020

gaggtctcaa aaattgtagc atctatgtgg gacagccttg gagaagaaca aaagcaggta   1080

tataaaagga aaacagaagc tgccaaaaaa gaatacctga aggccctggc ggcatacagg   1140

gccagcctcg tttctaaggc tgctgctgag tcagcagaag cccagaccat ccgttctgtt   1200

cagcagaccc tggcgtcgac caatctaaca tcctctctcc ttctcaacac tccactgtct   1260

caacatggaa cagtgtcagc atcacctcag actctccagc aatccctccc taggtcaatc   1320

gctcccaaac ccttaaccat gagactcccc atgaaccaga ttgtcacatc agtcaccatt   1380

gcagccaaca tgccctcgaa cattggggct ccactgataa gctccatggg aacgaccatg   1440

gttggctcag caccctccac ccaagtgagt ccttcggtgc aaacccagca gcatcagatg   1500

caattgcagc agcagcagca gcagcaacaa caacagatgc aacagatgca gcagcagcaa   1560

ctccagcagc accaaatgca tcagcaaatc cagcagcaga tgcagcagca gcatttccag   1620

caccacatgc agcagcacct gcagcagcag cagcagcatc tccagcagca aattaatcaa   1680

cagcagctgc agcagcagct gcagcagcgc ctccagctgc agcagctgca acacatgcag   1740

caccagtctc agccttctcc tcggcagcac tcccctgtcg cctctcagat aacatccccc   1800

atccctgcca tcgggagccc ccagccagcc tctcagcagc accagtcgca aatacagtct   1860

cagacacaga ctcaagtatt atcgcaggct atacctacaa tatgtgaatc aaactgttta   1920

atgaatcctg ggacatactg atgactataa actggcctct ctgagtcata gaaaaatggc   1980

cttatttctc cagaagtgag taaaccacac ttccaggcta tctgaactcc tgaagcccta   2040
```

-continued aaaataaaaa gcacagttgt aactacctga aatatgaaga tccagtttca tacaaacatt 2100
tgtatgacgt gaatagttga tggcattttt ttgtcatgaa aaaaataatg taaatcacag 2160
acttttgcca aagctcttat tttttttcct aaatctctcc agaaaaaaaa tgcaagtgac 2220
taaattcaat tattgactaa tttccacttt ttatccatga cttctccaaa tcaaaccaca 2280
gtatatgttg taacaatatc tatgaccact gttagcccat tatattcatt ccaattagaa 2340
gaaatgtgaa tactatattc cgtgttttga gtgacaagtt tcgaaaaata aaaacactgt 2400
atttttaaaa gggaaatgca cttaaatgaa aacagttatt acaaaagtta agatttaaaa 2460
agaaaaagca agagttttta ttatgatgta ataccagtag aatatttaaa aggcacacca 2520
catctgaata atcaatgtaa atattttctt tcaaagttgt aagttttcat atcatgtgct 2580
gtaaagtttt cctaaatgag gctttaacgt aaacactggt gacataaacc attcattgct 2640
acgttgctta ttgtgttttt atgctgtttt atactttttt atgagttatg atagcagcaa 2700
ttaagttgtt tgtattttgc ttaactaaaa caaaaatgct tttatcttgc tatagaataa 2760
acacatttca gtaaaaactg tggactgtat tttgatgcaa caacaaagaa actgttcact 2820
tttcaaataa aatgatatgt cagatttca 2849

<210> SEQ ID NO 5
<211> LENGTH: 571
<212> TYPE: PRT
<213> ORGANISM: Homo sapiens

<400> SEQUENCE: 5

Met Lys Cys Gln Pro Arg Ser Gly Ala Arg Arg Ile Glu Glu Arg Leu
1 5 10 15

His Tyr Leu Ile Thr Thr Tyr Leu Lys Phe Gly Asn Asn Asn Asn Tyr
20 25 30

Met Asn Met Ala Glu Ala Asn Asn Ala Phe Phe Ala Ala Ser Glu Thr
35 40 45

Phe His Thr Pro Ser Leu Gly Asp Glu Glu Phe Glu Ile Pro Pro Ile
50 55 60

Thr Pro Pro Pro Glu Ser Asp Pro Ala Leu Gly Met Pro Asp Val Leu
65 70 75 80

Leu Pro Phe Gln Ala Leu Ser Asp Pro Leu Pro Ser Gln Gly Ser Glu
85 90 95

Phe Thr Pro Gln Phe Pro Pro Gln Ser Leu Asp Leu Pro Ser Ile Thr
100 105 110

Ile Ser Arg Asn Leu Val Glu Gln Asp Gly Val Leu His Ser Ser Gly
115 120 125

Leu His Met Asp Gln Ser His Thr Gln Val Ser Gln Tyr Arg Gln Asp
130 135 140

Pro Ser Leu Ile Met Arg Ser Ile Val His Met Thr Asp Ala Ala Arg
145 150 155 160

Ser Gly Val Met Pro Pro Ala Gln Leu Thr Thr Ile Asn Gln Ser Gln
165 170 175

Leu Ser Ala Gln Leu Gly Leu Asn Leu Gly Gly Ala Ser Met Pro His
180 185 190

Thr Ser Pro Ser Pro Pro Ala Ser Lys Ser Ala Thr Pro Ser Pro Ser
195 200 205

Ser Ser Ile Asn Glu Glu Asp Ala Asp Glu Ala Asn Arg Ala Ile Gly
210 215 220

Glu Lys Arg Ala Ala Pro Asp Ser Gly Lys Lys Pro Lys Thr Pro Lys

-continued

```
225                 230                 235                 240

Lys Lys Lys Lys Lys Asp Pro Asn Glu Pro Gln Lys Pro Val Ser Ala
                245                 250                 255

Tyr Ala Leu Phe Phe Arg Asp Thr Gln Ala Ala Ile Lys Gly Gln Asn
            260                 265                 270

Pro Asn Ala Thr Phe Gly Glu Val Ser Lys Ile Val Ala Ser Met Trp
        275                 280                 285

Asp Ser Leu Gly Glu Glu Gln Lys Gln Val Tyr Lys Arg Lys Thr Glu
    290                 295                 300

Ala Ala Lys Lys Glu Tyr Leu Lys Ala Leu Ala Ala Tyr Arg Ala Ser
305                 310                 315                 320

Leu Val Ser Lys Ala Ala Ala Glu Ser Ala Glu Ala Gln Thr Ile Arg
                325                 330                 335

Ser Val Gln Gln Thr Leu Ala Ser Thr Asn Leu Thr Ser Ser Leu Leu
            340                 345                 350

Leu Asn Thr Pro Leu Ser Gln His Gly Thr Val Ser Ala Ser Pro Gln
        355                 360                 365

Thr Leu Gln Gln Ser Leu Pro Arg Ser Ile Ala Pro Lys Pro Leu Thr
    370                 375                 380

Met Arg Leu Pro Met Asn Gln Ile Val Thr Ser Val Thr Ile Ala Ala
385                 390                 395                 400

Asn Met Pro Ser Asn Ile Gly Ala Pro Leu Ile Ser Ser Met Gly Thr
                405                 410                 415

Thr Met Val Gly Ser Ala Pro Ser Thr Gln Val Ser Pro Ser Val Gln
            420                 425                 430

Thr Gln Gln His Gln Met Gln Leu Gln Gln Gln Gln Gln Gln Gln Gln
        435                 440                 445

Gln Gln Met Gln Gln Met Gln Gln Gln Gln Leu Gln Gln His Gln Met
    450                 455                 460

His Gln Gln Ile Gln Gln Gln Met Gln Gln Gln His Phe Gln His His
465                 470                 475                 480

Met Gln Gln His Leu Gln Gln Gln Gln Gln His Leu Gln Gln Gln Ile
                485                 490                 495

Asn Gln Gln Gln Leu Gln Gln Gln Leu Gln Gln Arg Leu Gln Leu Gln
            500                 505                 510

Gln Leu Gln His Met Gln His Gln Ser Gln Pro Ser Pro Arg Gln His
        515                 520                 525

Ser Pro Val Ala Ser Gln Ile Thr Ser Pro Ile Pro Ala Ile Gly Ser
    530                 535                 540

Pro Gln Pro Ala Ser Gln Gln His Gln Ser Gln Ile Gln Ser Gln Thr
545                 550                 555                 560

Gln Thr Gln Val Leu Ser Gln Val Ser Ile Phe
                565                 570


<210> SEQ ID NO 6
<211> LENGTH: 3123
<212> TYPE: DNA
<213> ORGANISM: Homo sapiens

<400> SEQUENCE: 6

gaaccgacac gaggcttcac ctgggaagct tcaagtctgc ctacctgtga aaggtcaggc      60

cccaacaccc cttctgggaa atcctacagc taggatgcat ttctctcact gaaccccatc     120

cagcagagga cagaagagtc agaagagggt agagaggatt tagatactca tagaagatgt     180
```

-continued

```
agtggaggat gaagtgccaa cctcgctcgg gagccaggcg cattgaggag agacttcatt    240
acctgataac tacctatctg aaatttggaa ataataataa ctatatgaat atggctgagg    300
cgaacaatgc gttcttcgct gccagtgaga cattccacac accaagcctt ggggacgagg    360
aattcgaaat tccaccaatc acgcctcctc cagagtcaga ccctgcccta ggcatgccgg    420
atgtactgct accctttcaa gccctcagcg atccattgcc ttcccaggga agtgaattca    480
caccccagtt tccccctcaa agcctggacc tcccttccat tacaatctca agaaatctcg    540
tggaacaaga tggcgtgctt catagcagtg ggttgcatat ggatcagagc cacacacaag    600
tgtcccagta ccggcaggat ccctccctga tcatgcggtc catcgtccac atgaccgatg    660
ctgcgcgttc tggggtcatg cctcctgccc agctcaccac catcaaccag tctcagctca    720
gcgcccagtt ggggttgaat ttgggaggtg ccagtatgcc tcacacatct ccttcacctc    780
cagcaagcaa atcagccact ccctcccctt ccagctccat caatgaagag gatgctgatg    840
aagccaacag agccattgga gagaaaagag ctgctccaga ctctggcaag aagcccaaga    900
ctccaaagaa aaagaaaaag aaagatccca atgagccaca gaagccagtg tcagcatatg    960
ccctgttttt cagagacaca caggctgcaa ttaaaggtca aaaccccaat gcaacctttg   1020
gagaggtctc aaaaattgta gcatctatgt gggacagcct tggagaagaa caaaagcagg   1080
tatataaaag gaaaacagaa gctgccaaaa aagaatacct gaaggccctg gcggcataca   1140
gggccagcct cgtttctaag gctgctgctg agtcagcaga agcccagacc atccgttctg   1200
ttcagcagac cctggcgtcg accaatctaa catcctctct ccttctcaac actccactgt   1260
ctcaacatgg aacagtgtca gcatcacctc agactctcca gcaatccctc cctaggtcaa   1320
tcgctcccaa acccttaacc atgagactcc ccatgaacca gattgtcaca tcagtcacca   1380
ttgcagccaa catgccctcg aacattgggg ctccactgat aagctccatg ggaacgacca   1440
tggttggctc agcaccctcc acccaagtga gtccttcggt gcaaacccag cagcatcaga   1500
tgcaattgca gcagcagcag cagcagcaac aacaacagat gcaacagatg cagcagcagc   1560
aactccagca gcaccaaatg catcagcaaa tccagcagca gatgcagcag cagcatttcc   1620
agcaccacat gcagcagcac ctgcagcagc agcagcagca tctccagcag caaattaatc   1680
aacagcagct gcagcagcag ctgcagcagc gcctccagct gcagcagctg caacacatgc   1740
agcaccagtc tcagccttct cctcggcagc actcccctgt cgcctctcag ataacatccc   1800
ccatccctgc catcgggagc ccccagccag cctctcagca gcaccagtcg caaatacagt   1860
ctcagacaca gactcaagta ttatcgcagg tcagtatttt ctgaagacgc atatggcaga   1920
cggatttgcg tataccaagg agagtggcat aggagggaaa agcatatgtg gctgaaacct   1980
gtaagttggt gttggttatg cagaaatgtg taacagatca aacggtcctc tcaagtgtct   2040
attagatagg caataagaac tgcagtgtag ctgagtaaca tcttttagct gactataaat   2100
cactttgttt ttaaacaaga aaagctgtgc tcttttatgt gatgcctttt ttatttattc   2160
aggctatacc tacaatatgt gaatcaaact gtttaatgaa tcctgggaca tactgatgac   2220
tataaactgg cctctctgag tcatagaaaa atggccttat ttctccagaa gtgagtaaac   2280
cacacttcca ggctatctga actcctgaag ccctaaaaat aaaaagcaca gttgtaacta   2340
cctgaaatat gaagatccag tttcatacaa acatttgtat gacgtgaata gttgatggca   2400
ttttttgtc atgaaaaaaa taatgtaaat cacagacttt tgccaaagct cttatttttt   2460
ttcctaaatc tctccagaaa aaaaatgcaa gtgactaaat tcaattattg actaatttcc   2520
actttttatc catgacttct ccaaatcaaa ccacagtata tgttgtaaca atatctatga   2580
```

-continued

```
ccactgttag cccattatat tcattccaat tagaagaaat gtgaatacta tattccgtgt   2640

tttgagtgac aagtttcgaa aaataaaaac actgtatttt taaaagggaa atgcacttaa   2700

atgaaaacag ttattacaaa agttaagatt taaaaagaaa aagcaagagt ttttattatg   2760

atgtaatacc agtagaatat ttaaaaggca caccacatct gaataatcaa tgtaaatatt   2820

ttctttcaaa gttgtaagtt ttcatatcat gtgctgtaaa gttttcctaa atgaggcttt   2880

aacgtaaaca ctggtgacat aaaccattca ttgctacgtt gcttattgtg tttttatgct   2940

gttttatact tttttatgag ttatgatagc agcaattaag ttgtttgtat tttgcttaac   3000

taaaacaaaa atgcttttat cttgctatag aataaacaca tttcagtaaa aactgtggac   3060

tgtattttga tgcaacaaca aagaaactgt tcacttttca aataaaatga tatgtcagat   3120

ttc                                                                 3123


<210> SEQ ID NO 7
<211> LENGTH: 20
<212> TYPE: PRT
<213> ORGANISM: Homo sapiens

<400> SEQUENCE: 7

Asp Val Arg Phe Tyr Pro Ala Ala Ala Gly Asp Pro Ala Ser Leu Asp
1               5                   10                  15

Phe Ala Gln Cys
            20
```

TOX3 AS A BIOMARKER FOR BREAST CANCER

CROSS REFERENCE TO RELATED APPLICATIONS

This application is a continuation-in-part of, and includes a claim of priority under 35 U.S.C. §120 to, International Application No. PCT/US10/58795, filed Dec. 2, 2010, which designated the U.S. and that International Application was published under PCT Article 21(2) in English. This application also includes a claim of priority under 35 U.S.C. §119(e) to U.S. Provisional Application No. 61/266,918, filed Dec. 4, 2009.

FIELD OF THE INVENTION

The invention provides compositions and methods for detecting and/or modulating TOX3 gene expression and/or biological activity. Such compositions and methods find utility in the treatment of certain subsets of cancers, e.g. breast cancer.

BACKGROUND

Breast cancer remains a serious public health problem. Aside from skin cancer, breast cancer is the most common form of cancer in women, with a lifetime incidence rate in the US population of approximately 13%. Breast cancer also remains one of the top ten causes of death for women in the US, and the second leading cause of cancer deaths in this population. Like all forms of cancer, breast cancer can be considered as a molecular reprogramming of the normal cell. Thus, understanding the gene regulatory networks that exist in breast cancer cells is of fundamental importance.

While mutations in BRCA1 or BRCA2 genes impart a very high risk for development of breast cancer, such mutations exist in the population at low frequency (and generally act as recessive cancer genes), and thus cannot account for the majority of breast cancers. Mutations in other genes, including PT53, PTEN, STK11, CDH1, also impart significantly increased risk of disease. However, even together with BRCA1 and BRCA2, these mutations may only account for 20% of familial disease. Thus, multiple additional genetic factors account for the observed disease incidence. In addition, the complexity of disease means that there can be additive and synergistic effects of changes in other mediators, even in the context of BRCA1 and BRCA2 mutations as discussed herein.

Applicant identified, using microarray analysis, the early changes in gene expression in precursor thymocytes as they traversed a developmental checkpoint-termed positive selection. These studies led to identification of a gene encoding a nuclear protein subsequently designated TOX (Thymocyte selection-associated HMG-box protein). This protein contains a single centrally-located DNA binding motif known as an HMG-box, named after that found in canonical HMGB proteins. The HMG-box now defines a superfamily of proteins (which have 47 family members located in the human genome) that, despite diverse functions, share some general characteristics of DNA binding. HMG-box domains, including TOX, fold into three $\alpha$-helices that form a concave L-shaped structure that binds the minor groove of DNA. HMG-box proteins also bind distorted DNA structures and often can induce bending and unwinding of the DNA helix to fit the protein domain structure. Two general classes of HMG-box proteins have been identified based on their mode of binding to DNA; those that exhibit sequence-specific binding and those that bind DNA in a sequence-independent but structure-dependent fashion. The latter class of proteins includes the canonical HMGB proteins themselves, while the former include transcriptional regulators, such as LEF-1. Both kinds of proteins, however, play roles in regulating gene expression, often by inducing or stabilizing architectural changes in chromatin and facilitating nucleoprotein complex formation. HMG-box proteins may also augment other nuclear functions that benefit from architectural changes in DNA, including antigen receptor gene rearrangement and chromatin remodeling. By inspection of key residues in the HMG-box domain (TOX-box), TOX is almost certainly a member of the sequence-independent DNA-binding family. O'Flaherty E and Kaye J., TOX defines a conserved subfamily of HMG-box proteins. *BMC Genomics.* 2003; 4(1):13.

In this case, TOX may be targeted by recognizing structural features of chromatin or, alternatively, by binding to other proteins. The TOX-box also defines a subfamily of proteins that includes three additional members (TOX2, 3, and 4). Wilkinson B, et al., *Nat Immunol.* 2002; 3(3):272-80. Based on a high degree of conservation of the TOX-box sequence, all family members are predicted to be sequence-independent DNA-binding factors. Outside of the DNA-binding domains, the N-terminal domains of family members are the next most similar, and this domain has transactivation activity. The C-terminal domains of the family members are most distinct and there is reason to think that they may function as interaction domains. Yuan S H, et al., TOX3 regulates calcium-dependent transcription in neurons. *Proc Natl Acad Sci USA.* 2009; 106(8):2909-14. The C-terminal domain of TOX3 particularly stands out from the rest of the family, as it is highly glutamine-rich.

TOX expression is tissue- and stage-specific (although not T cell specific), with the greatest expression observed in the thymus and markedly reduced expression in peripheral lymphoid tissues. Wilkinson B, et al., 2002. Detailed expression of other TOX family members, however, has been less well characterized. TOX2 has been reported to be expressed in rat ovarian granulosa cells and mouse retina. As described herein, Applicant discovered that expression of Tox4 mRNA to be fairly widespread. Overall, it appears that despite some overlap in tissue expression, different TOX family members may play greater or lesser roles in specific tissues. Applicant further discovered that even in the mouse brain, where Tox and Tox3 mRNA are both expressed, they have non-overlapping patterns of expression.

Applicant characterized mice deficient in TOX and showed that this nuclear factor is required for development of a number of key aspects of the immune system including development of CD4 T cells, lymph nodes, and NK cells. Aliahmad P and Kaye J., Development of all CD4 T lineages requires nuclear factor TOX. *J Exp Med.* 2008; 205(1):245-56. Together the data indicate that TOX is a key regulator of precursor cell differentiation in various contexts, presumably by regulating gene expression (FIG. 3). These results make it likely that other TOX family members will also be found to play important regulatory roles in various cellular contexts. The biological function of other TOX-family members in vivo has not been characterized. Recently, however, expression of TOX3 has been reported to link calcium signaling to c-fos regulation in isolated neurons.

SUMMARY OF THE INVENTION

The present invention provides, in one embodiment, modulators of TOX3. Inventive modulators include, but are not limited to, antisense molecules, antibodies or antibody fragments, proteins or polypeptides as well as small molecules. Inventive modulators include, but are not limited to, antisense molecules, antibodies or antibody fragments, proteins or polypeptides as well as small molecules. According to additional aspects, the present invention provides for the use of TOX3 nucleic acids and/or proteins to detect an increase in susceptibility to certain types of cancers, e.g. breast cancer. Additional aspects relate to transgenic mice that either overexpress or inducibly express the TOX3 protein.

DETAILED DESCRIPTION OF THE INVENTION

Figure 1:
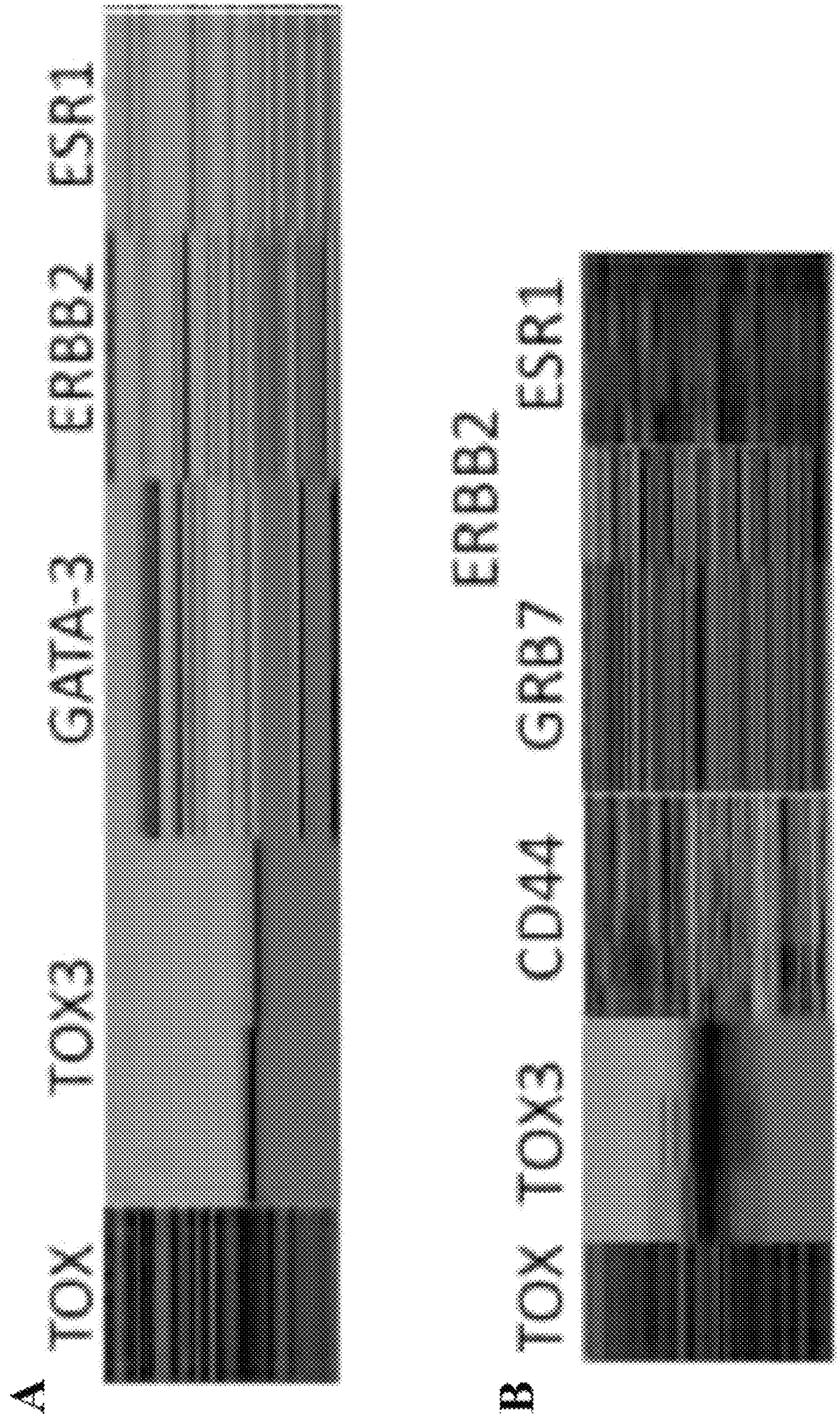
FIG. 1 shows the data collected from the microarray Database mining for expression of TOX3 by microarray. (A) Data analyzing 51 breast cancer cell lines (B) data analyzing 118 aggressively-treated early stage breast tumors (see text). Both sets of data are shown as heat maps, ordered based on expression of the TOX3 gene, with high to low expression shown bottom to top.

TOX3 is a member of the TOX family, which is a sub-group of the HMG-box of proteins. The HMG-box proteins are involved in binding to chromatin and altering transcription.

Applicant describes herein the involvement of TOX3 in certain subtypes of breast cancer. In particular, the present invention provides for TOX3 modulators. In addition, the present invention provides for the use of TOX3 nucleic acids and/or proteins to detect an increase in susceptibility to certain types of cancers, e.g. breast cancer.

Applicant realized that TOX3 (also known as TNRC9) has a role in breast cancer based on several key observations. Gene expression analysis was used to compare primary breast tumors from patients that were lymph node negative at the time of diagnosis but that had experienced relapse either to bone or to other parts of the body. Smid M, et al., Genes associated with breast cancer metastatic to bone. *J Clin Oncol.* 2006; 24(15):2261-7. Among the genes found to be upregulated in tumors that metastasized to bone was TOX3. More recently, two articles examined genome-wide association studies to identify breast cancer susceptibility loci, in particular searching for common low-penetrance alleles that would be associated with disease. Stacey S N, et al., Common variants on chromosomes 2q35 and 16q12 confer susceptibility to estrogen receptor-positive breast cancer. *Nat Genet.* 2007; 39(7):865-9. Easton D F, et al., Genome-wide association study identifies novel breast cancer susceptibility loci. *Nature.* 2007; 447(7148): 1087-93.

Both articles reported that SNPs linked to TOX3 were associated with increased breast cancer risk. Increased disease risk appears to be most associated with estrogen receptor positive tumors. Garcia-Closas M and Chanock S., Genetic susceptibility loci for breast cancer by estrogen receptor status. *Clin Cancer Res.* 2008; 14(24):8000-9. Estrogen positivity is a strong histopathological predictor of bone metastases, yielding a link between the two studies above. James J J, et al., Bone metastases from breast carcinoma: histopathological—radiological correlations and prognostic features. British *Journal of Cancer.* 2003; 89(4):660-5. Among a European population the risk allele was present in a homozygous state at a 7% frequency and imparted a 1.64 greater disease risk. Stacey et al., 2007. Among a small cohort of patients with familial breast cancer without BRCA1 and BRCA2 mutations, homozygotes for the TOX3 minor allele had a 2.4-fold increased cancer risk. Latif A, et al., Breast cancer susceptibility variants alter risks in familial disease. *J Med Genet.* 2010 February; 47(2):126-31. However, TOX3 has not been associated with increased risk of ovarian cancer, suggesting the potential for tissue specificity in its mode of action.

A retrospective study of microarray data reported that by ANOVA analysis TOX3 mRNA was upregulated in luminal A, luminal B, and ErbB2+ molecular subtypes of breast cancer tumors and downregulated in basal-like tumors, suggesting that TOX3 may not only play a biologically-relevant role in certain tumors but that expression may also have some value as a biomarker. Nordgard S H, et al., Genes harbouring susceptibility SNPs are differentially expressed in the breast cancer subtypes. *Breast Cancer Res.* 2007; 9(6):113. However, only statistical analysis was reported and not quantitative data on levels of expression. In another analysis of breast cancer patients, individuals homozygous for the TOX3 locus variant were more likely to be diagnosed before the age of 60 than those not homozygous for the TOX3 locus variant. Interestingly, minor allele frequencies for the TOX3-associated SNP were elevated among 40 human breast cancer cell lines. Surprisingly, however, there was no correlation between the allele and actual expression of TOX3 mRNA, although the range of expression levels for TOX3 among individual cell lines was quite broad in this report. According to particular aspects, a lack of an association between haplotype and TOX3 expression in these cell lines is due to TOX3's role during induction but not maintenance of tumors or additional changes in these cell lines as a result of extensive propagation in culture.

As mentioned above, BRCA1 or BRCA2 mutations can impart a very high risk for breast cancer. Interestingly, even among BRCA1 and BRCA2 mutation carriers, the minor allele SNP linked to TOX3 can impart an increased risk for disease, particularly for BRCA2 mutation carriers. Latif et al., 2009. This highlights the potential for additive or synergistic effects of disease susceptibility loci. In addition, the fact that cancers with BRCA2 mutations are more likely to be estrogen receptor positive than those with BRCA1 mutations is also consistent with the stronger association of TOX3 variation with estrogen receptor positive disease. At least in a cell line, however, expression of TOX3 itself was not estradiol responsive.

Together, the data strongly implicate TOX3 as playing a role in breast cancer. Based on Applicant's demonstration of the critical role of TOX in many cell fate decisions in the immune system, Applicant suggests that TOX3 has profound effects on regulation of cellular activity during initiation, maintenance, or spread of cancer.

Antibodies or Antibody Fragments

According to certain embodiments, peptides can be used to produce antibodies or similar TOX3 binding proteins. According to further embodiments, antibodies are useful to detect the presence of TOX3 in cells and tissue samples. In one embodiment, the antibody may be a rabbit polyconal antibody. In another embodiment, the antibody is AJ33 antibody. In another embodiment, the antibody is capable of distinguishing between tumor samples and non-tumor samples in a tissue microarray. One example of tissue microarrays (TMA) are those provided by National Cancer Institute Cancer Diagnosis Program (CDP), including progression TMA and prognostic TMA. In another embodiment, the antibody is capable of demonstrating the level of TOX3 expression in a sample obtained from a patient. In another embodiment, the patient is suspected of having cancer, including breast cancer. In another embodiment, the patient is suspected of having cancer based on the expression levels of other markers involved in breast cancer, such as BRCA1/2.

The present invention includes antibodies and/or antibody fragments that are effective in binding to TOX3. Suitable antibodies may be monoclonal or polyclonal antibodies. Antibodies may be derived by conventional hybridoma-based methodology, from antisera isolated from TOX3 inoculated animals or through recombinant DNA technology. Alternatively, inventive antibodies or antibody fragments may be identified in vitro by use of one or more of the readily available phage display libraries. Exemplary methods are well known in the art.

One embodiment of the present invention includes monoclonal antibodies that may be produced as follows. TOX3 protein may be produced, for example, by expression of TOX3 cDNA in a Baculovirus-based system. By this method, TOX3 cDNA or a fragment thereof is ligated into a suitable plasmid vector that is subsequently used to transfect Sf9 cells to facilitate protein production. In addition, it may be advantageous to incorporate an epitope tag or other moiety to facilitate affinity purification of the TOX3 protein. Clones of Sf9 cells expressing TOX3 are identified, e.g., by enzyme-linked immunosorbant assay (ELISA), lysates are prepared and the TOX3 protein purified by affinity chromatography and the purified protein is injected, intraperitoneally, into BALB/c mice to induce antibody production. It may be advantageous to add an adjuvant, such as Freund's adjuvant, to increase the resulting immune response.

Serum is tested for the production of specific antibodies and spleen cells from animals having a positive specific antibody titer are used for cell fusions with myeloma cells to generate hybridoma clones. Supernatants derived from hybridoma clones are tested for the presence of monoclonal antibodies having specificity against TOX3. For a general description of monoclonal antibody methodology, see, e.g., Harlow and Lane, *Antibodies: A Laboratory Manual*, Cold Spring Harbor Laboratory (1988).

In addition to the baculovirus expression system, other suitable bacterial or yeast expression systems may be employed for the expression of TOX3 protein or polypeptides thereof. As with the baculovirus system, it may be advantageous to utilize one of the commercially-available affinity tags to facilitate purification prior to inoculation of the animals. Thus, the TOX3 cDNA or fragment thereof may be isolated by, e.g., agarose gel purification and ligated in frame with a suitable tag protein such as 6-His, glutathione-S-transferase (GST) or other such readily available affinity tag. See, e.g., *Molecular Biotechnology: Principles and Applications of Recombinant DNA*, ASM Press pp. 160-161 (ed. Glick, B R and Pasternak, J J 1998).

According to certain embodiments, TOX3 peptides can be used to produce antibodies or similar TOX3 binding proteins. TOX3 peptides useful in producing antibodies can be made from the TOX3 polypeptide of SEQ ID NO:1 containing amino acids from about position 1 to about 576, from about position 1 to about 238, from about position 1 to about 150, from about position 2 to about 238, and from about position 2 to about 150. TOX3 peptides useful in producing antibodies can be made from the N-terminal portion of TOX3 polypeptide (SEQ ID NO:2) containing between 5 to 10 consecutive amino acids, containing between 5 to 15 consecutive amino acids, containing between 5 to 20 consecutive amino acids, containing between 5 to 25 consecutive amino acids, containing between 5 to 30 consecutive amino acids, containing between 5 to 35 consecutive amino acids, containing between 5 to 40 consecutive amino acids, containing between 5 to 45 consecutive amino acids, containing between 5 to 50 consecutive amino acids, containing between 5 to 55 consecutive amino acids, containing between 5 to 60 consecutive amino acids, containing between 5 to 65 consecutive amino acids, containing between 5 to 70 consecutive amino acids, containing between 5 to 75 consecutive amino acids, containing between 5 to 80 consecutive amino acids, containing between 5 to 85 consecutive amino acids, containing between 5 to 90 consecutive amino acids, containing between 5 to 95 consecutive amino acids, containing between 5 to 100 consecutive amino acids, containing between 5 to 105 consecutive amino acids, containing between 5 to 110 consecutive amino acids, containing between 5 to 115 consecutive amino acids, containing between 5 to 120 consecutive amino acids, containing between 5 to 125 consecutive amino acids, containing between 5 to 150 consecutive amino acids, containing between 5 to 175 consecutive amino acids, containing between 5 to 200 consecutive amino acids, and containing between 5 to 238 consecutive amino acids.

According to certain embodiments, TOX3 peptides can be used to produce antibodies or similar TOX3 binding proteins. TOX3 peptides useful in producing antibodies can be made from the TOX3 polypeptide containing amino acids. Examples of inventive peptides of length X (in amino acids), as indicated by polypeptide positions with reference to, e.g., SEQ ID NO:1, include those corresponding to sets of consecutively overlapping peptides of length X, where the peptides within each consecutively overlapping set (corresponding to a given X value) are defined as the finite set of Z peptides from amino acid positions:

$n$ to $(n+(X-1))$;

where n=1, 2, 3, . . . (Y−(X−1));

where Y equals the length (amino acid or base pairs); where X equals the common length (in amino acid) of each peptide in the set (e.g., X=10 for a set of consecutively overlapping 10-mers); and where the number (Z) of consecutively overlapping oligomers of length X for a given sequence of length Y is equal to Y−(X−1).

Examples of inventive 10-mer peptide within a sequence of length 576 amino acid residues include the following set of 576 oligomers, indicated by polypeptide positions 1-20, 2-21, 3-22, 4-23, 5-24 to 566-576.

The present invention encompasses, for each of SEQ ID NOS: 1 and SEQ ID NO: 2, multiple consecutively overlapping sets of peptides or modified peptides of length X, where, e.g., X=9, 10, 17, 20, 22, 23, 25, 27, 30, or 35 amino acids. For example SEQ ID NO: 7.

Preferred sets of such peptides or modified peptides of length X are those consecutively overlapping sets of oligomers corresponding to SEQ ID NOS:1 and SEQ ID NO:2.

Administration of TOX3 Modulators and Compositions Thereof

The present invention provides TOX3 modulators and compositions comprising one or more TOX3 modulator as well as methods that employ these inventive inhibitors in in vivo, ex vivo, and in vitro applications where it is advantageous to reduce or eliminate the expression or activity of TOX3 or a functionally-downstream molecule. TOX3 modulators may find use as drugs for supplementing cancer therapeutics and other agents. TOX3 modulators may also find use in other diseases of hyperproliferation.

Compositions may be administered parenterally, topically, orally, or locally for therapeutic treatment. Preferably, the compositions are administered orally or parenterally, i.e., intravenously, intraperitoneally, intradermally, or intramuscularly.

Inventive compositions will include one or more TOX3 modulator and may further comprise a pharmaceutically-acceptable carrier or excipient. A variety of aqueous carriers may be used, e.g., water, buffered water, 0.4% saline, 0.3% glycine, and the like, and may include other proteins for enhanced stability, such as albumin, lipoprotein, globulin, etc., subjected to mild chemical modifications or the like.

TOX3 modulators useful in the treatment of disease in mammals will often be prepared substantially free of naturally-occurring immunoglobulins or other biological molecules. Preferred TOX3 modulators will also exhibit minimal toxicity when administered to a mammal.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The selection of the appropriate method for administering TOX3 modulators of the present invention will depend on the nature of the application envisioned as well as the nature of the TOX3 modulator. Thus, for example, the precise methodology for administering a TOX3 modulator will depend upon whether it is an antisense molecule, a protein and/or peptide, an antibody or antibody fragment, or a small molecule. Other considerations include, for example, whether the TOX3 modulator will be used to regulate tumor cell initiation, growth, invasion, or metastasis, or as an adjunct to other cancer therapeutics.

A variety of methods are available in the art for the administration of antisense molecules. Exemplary methods include gene delivery techniques, including both viral and non-viral based methods as well as liposome-mediated delivery methods.

Gene delivery methodologies will be effective to, for example, reduce tumor cell proliferation, or supplement radiation and/or chemotherapeutic treatment of tumors. See, Wheldon, T E et al., *Radiother Oncol* 1998; 48(1):5-13 (gene delivery methodologies for enhancement of fractionated radiotherapy). By these methodologies, substantial therapeutic benefit may be achieved despite transfection efficiencies significantly less than 100%, transient retention of the transfected inhibitor, and/or existence of a subpopulation of target cells refractory to therapy.

Alternatively, gene delivery methodology may be used to directly knock-out endogenous TOX3 within tumor cells. For example, the TOX3 gene may be targeted by transfection of a gene delivery vector carrying a TOX3 modulator. Preferential transfection into or expression within tumor cells may be achieved through use of a tissue-specific or cell cycle-specific promoter, such as, e.g., promoters for BRCA2 or for immunoglobulin genes (Vile, R G et al., *Cancer Res.* 1993; 53:962-967 and Vile, R G, *Semin. Cancer Biol.* 1994; 5:437-443 or through the use of trophic viruses that are confined to particular organs or structures, such as, e.g., a replication selective and neurotrophic virus that can only infect proliferating cells in the central nervous system.

Thus, to achieve therapeutic benefit, TOX3 within the tumor cells should be preferentially modulated. This can be accomplished by transfecting a gene expressing a TOX3 inhibitor, a TOX3 antisense molecule, a TOX3 gene-specific repressor, or an inhibitor of the protein product of the TOX3 gene.

As used herein, the phrase "gene delivery vector" refers generally to a nucleic acid construct that carries and, within certain embodiments, is capable of directing the expression of an antisense molecule of interest, as described in, for example, *Molecular Biotechnology: Principles and Applications of Recombinant DNA*, Ch. 21, pp. 555-590 (ed. B P Glick and J J Pasternak, $2^{nd}$ ed. 1998); Jolly, Cancer *Gene*

*Ther.* 1994; 1:51-64; Kimura, *Human Gene Ther.* 1994; 5:845-852; Connelly, *Human Gene Ther.* 1995; 6:185-193; and Kaplitt, *Nat. Gen.* 1994; 6:148-153.

A number of virus- and non-virus-based gene delivery vector systems have been described that are suitable for the administration of TOX3 modulators. Virus-based gene delivery systems include, but are not limited to, retrovirus such as Moloney murine leukemia virus, spumaviruses, and lentiviruses; adenovirus; adeno-associated virus; and herpes-simplex virus vector systems. Viruses of each type are readily available from depositories or collections such as the American Type Culture Collection (ATCC; 10801 University Boulevard, Manassas, Va. 20110-2209) or may be isolated from known sources using commonly available materials and techniques.

The gene delivery vector systems of the present invention will find applications both in in vivo as well as ex vivo therapeutic regimens. Methods for gene delivery systems are well known in the art (e.g. retroviral gene delivery vector systems, adeno-associated viral gene delivery vector systems, and non-viral gene delivery vectors).

In various embodiments, the present invention includes an assay to detect the presence and level of TOX3, either an allele, a transcript, or protein as it relates to certain subsets of cancers (e.g. breast cancers). In various embodiments, the expression levels of between TOX3 transcript and/or protein is coincident with molecular subtypes of cancers. For example, in various embodiments, levels of TOX3 expression are higher or lower coincident with molecular breast cancer subtypes luminal A (lumA), luminal B (lumB), ErbB2-enriched, basal (basL), and normal-breast-like (normL), (mApo) and luminal C (lumC). According to particular aspects, the current invention encompasses a kit for detecting TOX3 polynucleotides and/or proteins.

Polynucleic Acid Detection.

There are many techniques readily available in the field for detecting the presence, absence, and/or level of an allele, transcript, or other biomarker, including mRNA microarrays. For example, enzymatic amplification of nucleic acid from an to individual may be used to obtain nucleic acid for subsequent analysis (e.g., polymerase chain reaction (PCR) and reverse transcriptase-PCR (RT PCR)). The presence or absence of allele, transcript or other biomarker may also be determined directly from the individual's nucleic acid without enzymatic amplification.

Analysis of the nucleic acid from an individual, whether amplified or not, may be performed using any of various techniques. Useful techniques include, without limitation, PCR-based analysis, sequence analysis, and electrophoretic analysis. As used herein, the term "nucleic acid" means a polynucleotide such as a single- or double-stranded DNA or RNA molecule including, for example, genomic DNA, cDNA, and mRNA. The term nucleic acid encompasses nucleic acid molecules of both natural and synthetic origin as well as molecules of linear, circular, or branched configuration representing either the sense or antisense strand, or both, of a native nucleic acid molecule.

Protein Detection and/or Biomarker Detection.

There are many techniques readily available in the field for detecting the presence or absence of polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method, or interferometry).

Similarly, there are any number of techniques that may be employed to isolate and/or fractionate biomarkers. For example, a biomarker may be captured using biospecific capture reagents, such as antibodies, aptamers, or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer, and hybrids of these.

Alternatively, for example, the presence of biomarkers such as polypeptides may be detected using traditional immunoassay techniques. Immunoassay requires biospecific capture reagents, such as antibodies, to capture the analytes. The assay may be designed to specifically distinguish protein and modified forms of protein, which can be done by employing a sandwich assay in which a first antibody captures more than one form and a second distinctly-labeled antibody specifically binds and provide distinct detection of the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or blood that may interfere with detection. Fractionation may include platelet isolation from other blood components, sub-cellular fractionation of platelet components, and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface to which a capture reagent (also called an adsorbent or affinity reagent) is attached. Frequently, the surface of a biochip comprises a plurality of addressable locations, each of which has the capture reagent bound there.

Microarray Analysis.

Applicant examined existing microarray data and determined the presence of TOX3 transcript in breast cancer cell lines and tumors. This analysis is a critical first step to take these studies beyond SNP associations. It should be noted that the expression of TOX3 appears to be relatively restricted in normal tissues, with highest levels of expression in fetal brain (BioGPS; http://biogps.gnf.org). As shown in FIG. 1, Applicant analyzed two microarray studies, organizing heat maps based on expression of TOX3 (UCSC Cancer Genomics Browser). Neve R M, et al., A collection of breast cancer cell lines for the study of functionally distinct cancer subtypes.

*Cancer Cell.* 2006; 10(6):515-27. Chin K, et al., Genomic and transcriptional aberrations linked to breast cancer pathophysiologies. *Cancer Cell.* 2006; 10(6):529-41. Interestingly, expression of TOX3 dramatically subsets both cell lines and tumors into high and low expressers. Applicant determined that TOX3 may act as a novel marker to subset tumors. Applicant compared this same ordered data set with expression of other select genes, including TOX itself. Results from this analysis include a number of interesting and surprising points. In both tumors and cell lines there appears to be an inverse correlation between expression of TOX and TOX3. According to particular aspects, based on the near identity of the DNA-binding domains and the differences elsewhere in these proteins, these two family members in essence act as dominant negative mutants of each other (i.e. compete for DNA binding but have different functions). In addition, there is a positive, although not absolute, correlation between estrogen receptor (ESR1) expression and TOX3 expression. This would be consistent with a more dominant role for TOX3 in ER+ disease, as discussed above. The transcription factor GATA3 is often coexpressed with estrogen receptor alpha in breast cancer cells and is one molecular marker of the luminal A subtype of breast cancer. In addition, there is an overall positive correlation between GATA3 and TOX3 expression in the cell lines studied. In general, there is a positive correlation between TOX3 expression and ERBB2 and GRB7 expression (the latter analyzed for tumors). GRB7 is an SH2-domain adaptor protein that binds to receptor tyrosine kinases and is genetically linked to the ERBB2 (HER2/neu) proto-oncogene. ERBB2 and GRB7 are commonly co-amplified in breast cancers. Interestingly, in an analysis that examined the expression of CD44 and TOX3, Applicant discovered that there was an inverse correlation between expression of CD44 and TOX3, which is consistent with poor expression of TOX3 in the basal subtype (CD44 has been suggested as one marker for cancer stem cells and expression of CD44 may be associated with basal-like disease. Finally, Applicant found no association with c-fos, distinguishing the possible action of TOX3 in breast cancer from that observed in neurons. There is certainly cellular heterogeneity within all these samples and thus expression of these genes on a per cell basis is unknown.

Figure 2:
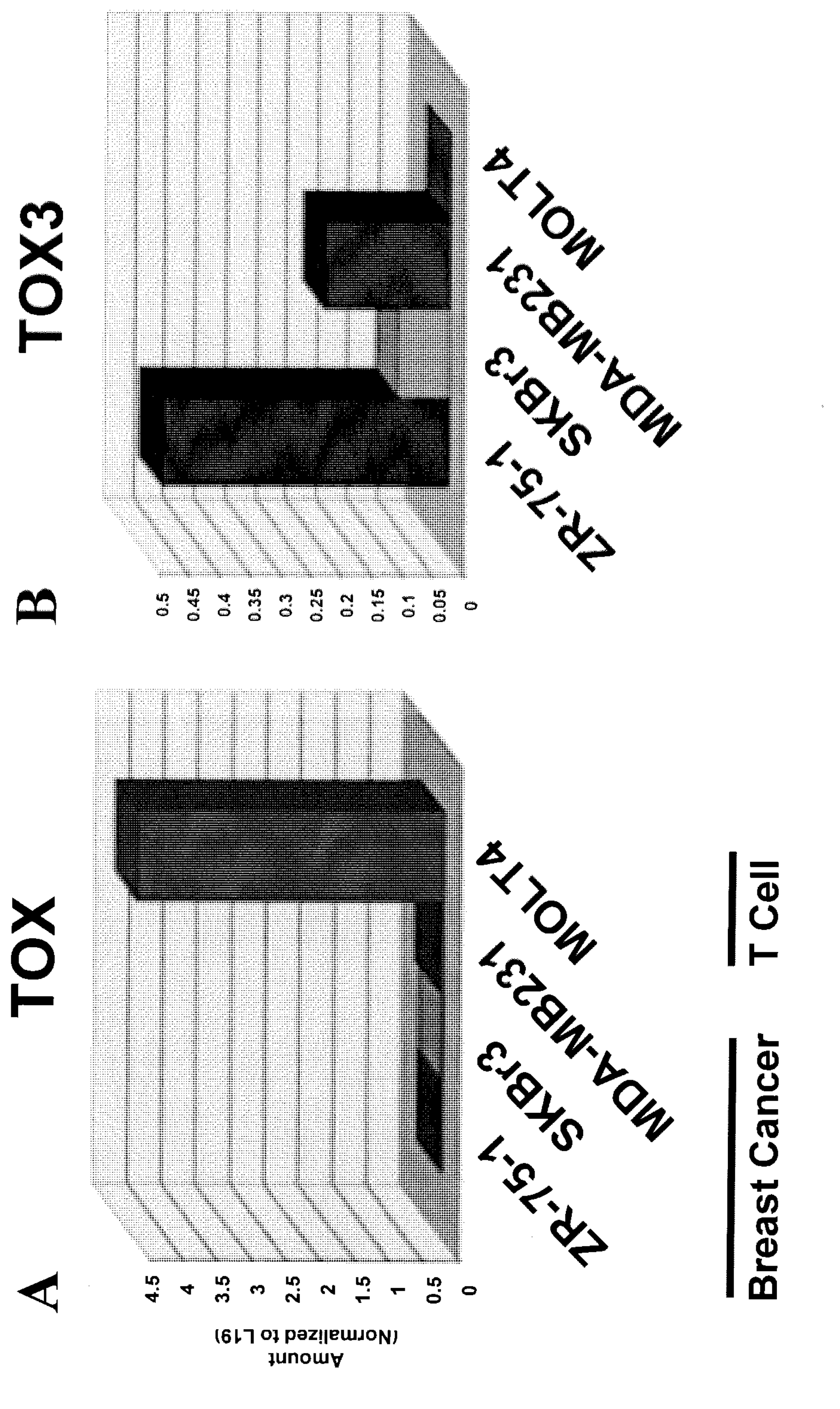
FIG. 2 demonstrates the expression of (A) TOX and (B) TOX3 in human cell lines using quantitative RT-PCR for expression of TOX or TOX3, as indicated, in (L to R) breast cancer cell lines, ZR-75-1, SKBr3, MDA-MB231 and T-Cell line, MOLT4, normalized to expression of the MRPL19 housekeeping gene.

TOX3 gene expression in breast cancer cell lines and tumors. Applicant examined directly whether TOX3 is expressed in breast cancer cells using quantitative RT-PCR. MOLT4, an oft-studied human acute lymphoblastic leukemia cell line highly expressed TOX but not TOX3 (FIG. 2). In contrast, three oft-studied breast cancer cell lines expressed TOX3 to various levels, but did not express TOX (FIG. 2). Interestingly, ZR75-1, the highest expresser, is an ER+ luminal subtype of breast cancer cell. These results are consistent with the role of TOX in the immune system and the role of TOX3 in breast cancer. Moreover, since the tissue microenvironment can greatly influence cancer cells and microarray analysis of tumors includes a heterogeneous population of cells, this result confirms expression of TOX3 by the cancer cell itself.

In Vivo Model of TOX3 Expression

As described herein, the present invention provides an animal model for a disease and/or condition, including a transgenic animal that expresses a TOX protein. In some embodiments, the TOX protein is TOX3. In some embodiments, the animal is a rodent. In some embodiments, the animal is a mouse or a rat. In some embodiments, the disease and/or condition is cancer. In other embodiments, the disease and/or condition is breast cancer.

In other embodiments, the TOX expression is specific to a cell type. In some embodiments, the cell type is a breast tissue cell. In some embodiments, the breast tissue cell is of the duct and/or lobule. In other embodiments, the cell type also expresses a fluorescent marker. In other embodiments, the marker is green fluorescent protein (GFP), enhanced green fluorescent protein (EGFP), red fluorescent protein (RFP), blue fluorescent protein (BFP), yellow fluorescent protein (YFP), GFP-luciferase fusion protein. In some embodiments, the TOX expression is constitutively expressed. In some embodiments, the TOX expression is under the control of a tissue specific promoter. In some embodiments, the expression of TOX protein is higher in the transgenic animal when compared to wild-type control. In some other embodiments, the TOX expression is induced following administration of a reagent including, for example, a tetracycline inducible cre-loxP system. In some embodiments, the TOX protein is TOX3.

As further described herein, the present invention provides a method of preparing a transgenic animal expressing a TOX protein, such as TOX3, including providing a transgenic construct. In some embodiments, the transgenic construct allows for constitutive expression of the TOX protein, such as TOX3, by including a TOX protein cassette, such as a TOX3 cassette encoding one or more of SEQ ID NO.: 1, 2, 3, or 4. In other embodiments, the tissue specific promoter is operatively linked to a TOX protein cassette, such as a TOX3 cassette encoding one or more of SEQ ID NO.: 1, 2, 3, or 4. In some embodiments, generating a transgenic animal expressing a TOX protein, such as TOX3, includes injecting the transgenic construct into a pronucleus. In some embodiments, the rodent is of a specific strain, such as a FVB/N mouse. In other embodiments, the transgenic construct further includes the MMTV promoter. In other embodiment, the transgenic animal is generated by establishing founder progeny including cre-inducible TOX protein expressing animals, and MMTV-cre expressing animals, and cross-mating MMTV and TOX expressing animals for tissue specific induction. In some embodiments, the tissue specific induction is in breast tissue. In other embodiments, the transgenic construct further includes a marker such as green fluorescent protein (GFP), enhanced green fluorescent protein (EGFP), red fluorescent protein (RFP), blue fluorescent protein (BFP), yellow fluorescent protein (YFP), or GFP-luciferase fusion protein. In other embodiments, the transgenic construct contains an IRES element. In other embodiments, the transgenic construct allows for bi-cistronic expression. In some embodiments, the expression of TOX protein is higher in the transgenic animal when compared to wild-type control.

In other embodiments, the transgenic construct contains a sequence containing about 70%, 75%, 80%, 85%, 90%, 95%, or 99% or more sequence similarity to SEQ ID NO: 1, SEQ ID NO: 2, SEQ ID NO: 3, SEQ ID NO: 4. In other embodiments, the transgenic construct contains a sequence containing about 70%, 75%, 80%, 85%, 90%, 95%, or 99% or more sequence similarity to a nucleotide sequence encoded by TOX3. In other embodiments, TOX3 is mouse, rat, or human TOX3.

In other embodiments, the transgenic animal expressing a TOX protein, such as a rodent, exhibit enhanced characteristics of breast cancer pathogenesis, compared to a wild-type control. In some embodiments, characteristics of breast cancer pathogenesis include focal mammary tumors, multifocal disease involving the whole epithelium, enhanced branch formation and/or fat pad invasion. In other embodiments, cells isolated from the transgenic animal display enhanced migration in a matrigel invasion assay. In some embodiments, the rodent is a mouse. In some embodiments, the rodent is of a specific strain, such as FVB/N. In other embodiments, In some embodiments, the TOX protein is TOX3.

The present invention also provides a method of drug screening including providing a model comprising a quantity of cells constitutively expressing TOX3, a transgenic animal that overexpresses TOX3, or a transgenic animal for which TOX3 expression may be induced, including in tissue-specific compartments, administering one or more drugs to the model, and detecting a change in the model to determine if the one or more drugs has an effect of interest on the model. In one embodiment, the transgenic animal is a MMTV-huTOX3 Tg mouse. In some embodiments, the cells expressing TOX3 also express a fluorescent marker. In some embodiments, the fluorescent marker is green fluorescent protein (GFP), enhanced green fluorescent protein (EGFP), red fluorescent protein (RFP), blue fluorescent protein (BFP), yellow fluorescent protein (YFP), or GFP-luciferase fusion protein. The present invention also provides a method of drug screening including providing an animal model as described herein, administering one or more drugs to the animal, and detecting a change in or reaction by the animal to determine if the drug has an effect of interest.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

TOX3 is Highly Expressed in Certain Subsets of Breast Cancer Tumors

Figure 4:
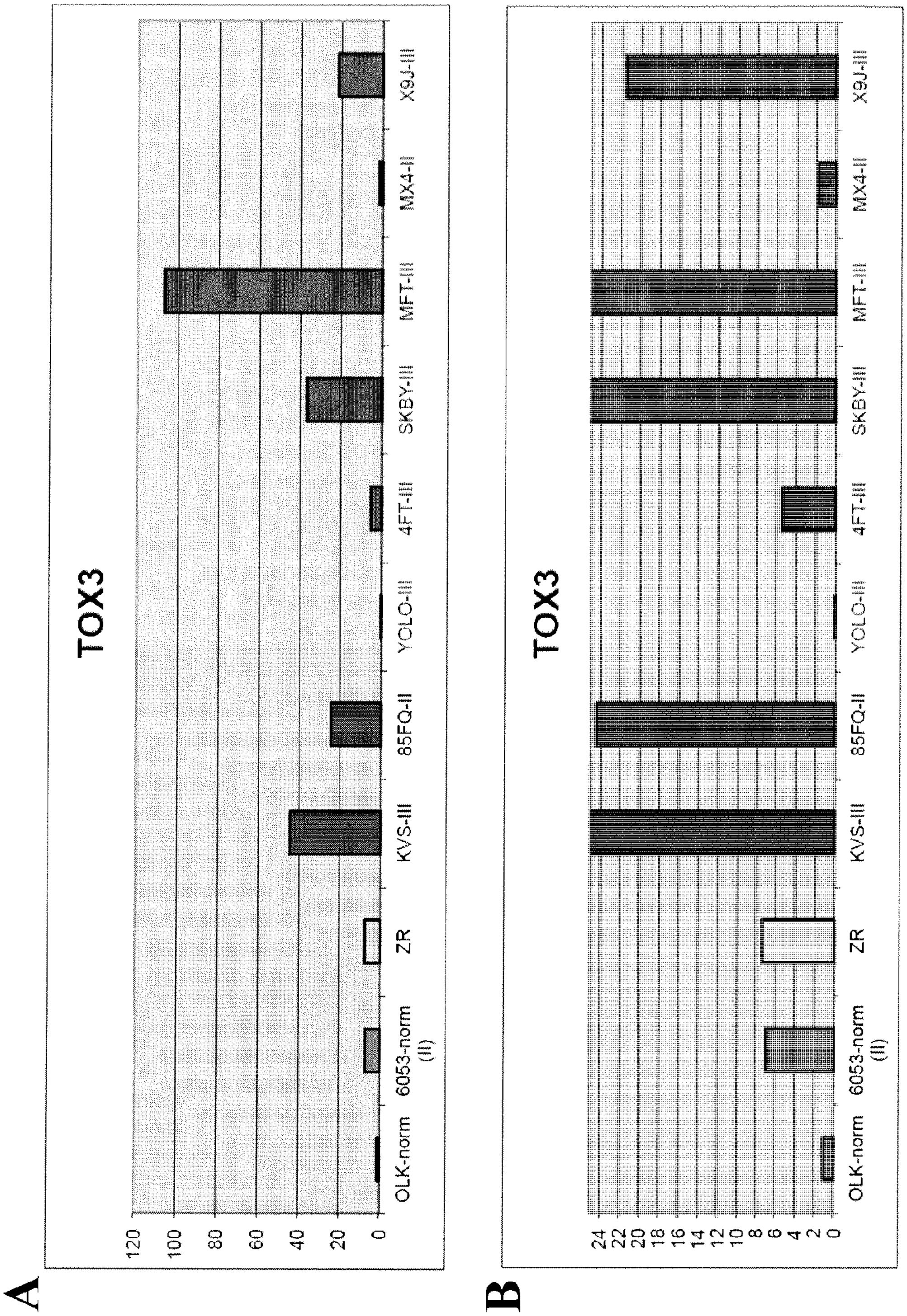
FIG. 4 shows TOX3 expression in breast cancer. The top panel (A) shows a quantitative RT-PCR experiment for TOX3 expression in breast tumors, as in FIG. 2. Normal breast tissue samples are in blue, breast cancer cell line ZR75-1 in yellow, and tumor samples in red. The normal sample derived from a non-cancer patient was arbitrarily set to 1. The bottom panel (B) shows the same data plotted with a reduced scale on the y-axis.

In this Example, Applicant determined that TOX3 is highly expressed in certain subsets of breast cancer tumors. Applicant analyzed TOX3 expression by qRT-PCR in RNA derived from 8 breast cancer tumors and 2 normal breast tissue samples; all samples were obtained from a commercial source. The breast cancer RNA samples were pre-selected by the following minimal criteria; the patients were (1) female, (2) White/Caucasian, and (3) had been diagnosed with estrogen receptor positive disease. All tumors were stage II or stage III infiltrating ducal carcinomas, from patients aged 41 to 78 years of age. For the two normal samples, one was from a 46-year-old patient who did not have cancer and one was derived from normal tissue from a 73-year-old patient diagnosed with stage II breast cancer. Applicant normalized the results to the sample from the non-cancer patient, arbitrarily assigning a value of 1 (FIG. 4). Surprisingly, the second "normal" sample had a 7-fold increase in TOX3 expression, similar to that seen in the ZR75-1 breast cancer cell line. According to certain embodiments, this result is related to the fact that this sample was derived from a cancer patient, and thus reflects an inherent variability in normal expression of this gene. Interestingly, there was great variability in expression of TOX3 among these tumor samples, ranging from well below that even detected in the normal tissue to greater than 100-fold upregulated in one tumor sample (MFT). This is reminiscent of the microarray data described above. According to certain embodiments, these expression differences correlate with TOX3 locus allelic differences. Intriguingly, though, only two of the eight patients had reported that their mothers also had breast cancer, and these were among the top three expressers of TOX3 (samples MFT and SKBY).

Example 2

The Predominant TOX3 Transcript in Breast Cancer Cell Lines and Tumors is the Longer Variant 1

Figure 5:
FIG. 5 demonstrates the TOX3 splice form variants that predominate in breast cancer. (A) shows predicted amino acid sequences of the N-terminus encoded by variant forms of TOX3 mRNA. Gray indicates identity (variants encoded by SEQ ID NO: 1 and SEQ ID NO: 5 are identical throughout subsequent C-terminal sequence, not shown). (B) shows the results from the RT-PCR experiment analyzing for variant forms of TOX3, as indicated. Specific primer designs for each variant allow detection a amplification of a 170 base pair fragment unique to variant 1 encoded by SEQ ID NO: 4, and amplification of a 186 base pair fragment for variant 2 encoded by SEQ ID NO: 6. Analysis includes a breast cancer cell line (ZR75-1) as well as a breast cancer tumor (BC.MFT) that Applicant found to express high levels of TOX3 mRNA (see FIG. 4). (C) Western blot detection using novel rabbit monoclonal anti-TOX3 antibody AJ33 specifically identifies TOX3 in HEK-293 or MCF-7 cell lines transfected with vector control or TOX3 vector in as indicated. (D) Various depictions of normal, non-tumor samples, wherein anti-TOX3 AJ33 antibody staining does not show TOX3 staining (E) In various tumor samples, AJ33 detection of TOX3 results in dark compact intracellular positive staining.
Figure 5:
Figure 5:
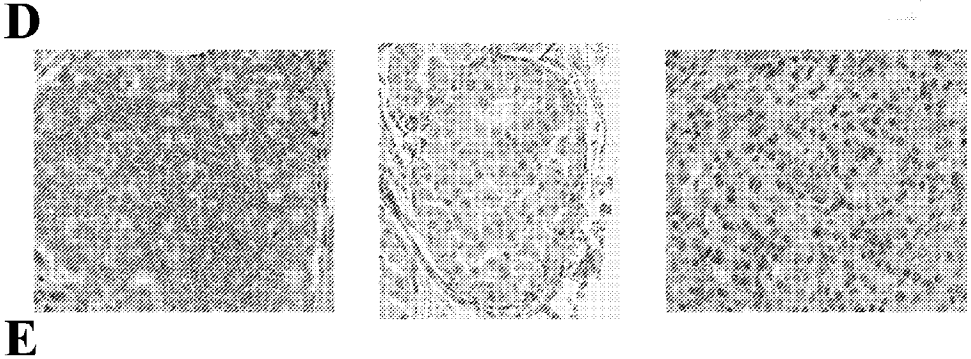
Figure 5:
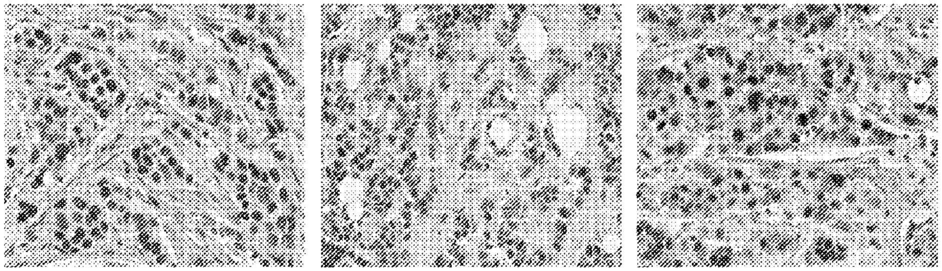

In this Example, for the first time the Applicant examined the predominant TOX3 splice variant in breast cancer cell lines and tumors. Two TOX3 transcripts have been reported that encode different N-terminal ends of the protein (FIG. 5A). The shorter variant 2 includes an alternative exon within the otherwise first intron of the TOX3 locus. To accomplish this experiment, Applicant designed a common 3' primer and distinct 5' primers that allowed the two transcripts to be distinguished. These were used in end point RT-PCR on RNA derived from the ZR75.1 cell line and the MFT breast cancer tumor (see above). Results indicated that variant 1 is the predominant transcript, even in primary tumor cells (FIG. 5B). Thus, the in vivo work will focus on this form of the protein.

Example 3

Breast Cancer Tumors that Highly Express TOX3 are Analyzed Via Transcriptome Analysis In this Example, the Applicant analyzed breast cancer tumors that highly express TOX3 using transcriptome. Global expression analysis has enabled classification of molecularly-defined subsets of cancers. For breast cancer, five subtypes: luminal A, luminal B, Erbb2-enriched, basal, and normal-breast-like, were proposed based on gene expression clusters that were relatively stable over time and have some clinical correlations. However, such classifications also belie the complexity and heterogeneity of the disease even within subtypes. Indeed, a subsequent large real-time RT-PCR analysis proposed twelve disease subtypes, based on expression of 47 genes. Chanrion M, et al., A new molecular breast cancer subclass defined from a large scale real-time quantitative RT-PCR study. BMC Cancer. 2007; 7:39. In addition, in terms of individual genes, this classification does not necessarily separate out important functional components of tumor formation or maintenance, which may be shared among subtypes, from useful but not necessarily causative biomarkers. As elaborated above, Applicant proposes to identify TOX3 as a disease susceptibility locus.

Applicant's preliminary data indicates that high level of expression of TOX3 may not fit neatly into otherwise defined subtypes. To address this issue, global gene expression analysis by microarray is performed to compare tumors with very high TOX3 expression and tumors with very low TOX3 expression (See, FIG. 4). While a small number of samples cannot be used to define a new molecular subtype, Applicant can use this data to narrow the number of genes that may be proximal gene targets of TOX3. In addition, the data for expression of genes that have been previously used to define subtypes is examined to see how these samples fall within those groups. While much microarray analysis is dependent on calls of relatively modest changes in gene expression, Applicant will take a much more stringent approach. As TOX3 is a transcriptional regulator, Applicant will implement a simplistic approach labeling genes that are highly expressed in the absence or presence of TOX3 as unlikely TOX3 gene targets and thus will not be investigated further.

Those genes whose expression is shared in TOX3 high cells (or show correlation with levels of TOX3 expression) and whose expression is absent or low in tumors that express little TOX3 are first examined. For that reason, quantitative data on TOX3 from Applicant's qRT-PCR are used initially. The high degree of genome annotation makes it likely that sorting through even a larger number of genes looking for known regulators of cell growth, survival, differentiation, or gene regulation that are good candidates for follow-up as potential TOX3 gene targets in the context of breast cancer.

Example 4

The Molecular and Cellular Effects of Manipulating TOX3 Expression in Breast Cancer In this Example, the molecular and cellular effects of manipulating TOX3 expression in breast cancer are examined using the ZR75-1 cell line that expresses TOX3 in a complementary approach. ZR75-1 cells previously have been reported to be transfectable and susceptible to siRNA-mediated knockdown. Thus using siRNA-mediated TOX3 knockdown Applicant can determine directly whether expression of candidate genes is modulated by expression of TOX3. Therefore, this analysis is accomplished on a global level via microarray, and is used as comparison with the data set obtained from primary tumor samples as above. Importantly, Applicant will determine if knockdown of TOX3 alters the growth, adhesion, or morphologic characteristics of this cell line, including the migration and invasion properties of the cells as assessed in vitro. Similarly, TOX3 is over-expressed in these cells to test for complementary changes in cellular behavior or gene expression. If we can detect differences upon loss of TOX3 in these cells we can also use this platform to test our hypothesis that TOX might act as a dominant negative of TOX3 function in this cellular context. This could provide the basis for thinking of ways to manipulate TOX3 activity, rather than expression. Together, these studies represent a powerful approach to identify gene targets of TOX3 and correlate that with cell behavior, as well as expression in primary tumors. This result indicates that TOX3 activation can be manipulated by overexpressing TOX in breast cancer tumors.

Example 5

Production of Anti-TOX3 Antibodies

In this Example, the Applicant examines the processes for developing an anti-TOX3 antibody, which is an essential reagent for the experiments described herein. To achieve this the Applicant has produced an excellent rabbit polyclonal antibody against TOX. This anti-TOX3 antibody was named AJ33. Polyclonal antibodies may be batch-specific in terms of affinity and titer, and by nature less specific than monoclonal antibodies. Utilizing recent advances in production of rabbit monoclonal antibodies, a novel monoclonal antibody raised against TOX3 can also be produced.

An anti-TOX3 antibody, such as AJ33, is invaluable in characterizing expression of TOX3 in breast cancer tumors. There are large numbers of well-characterized tissue arrays available for breast cancer (i.e. of known histological appearance and grade, metastatic properties, hormone receptor expression, and Her2 expression), some including adjacent normal tissue. Thus, analogous to the molecular subtyping approach, one can apply a TOX3 specific antibody to determine the expression pattern of TOX in tumors at the protein level. Since these will be fixed samples, initially an anti-peptide antibody that is likely to recognize denatured protein (and thus will also be useful for immunoblotting) is used. In addition, use of the N-terminal regions of the protein as a peptide source, which will allow discrimination from other family members, avoiding the highly conserved DNA binding domain and the Q-rich C-terminal domain. The resulting TOX3 rabbit polyclonal antibody, named AJ33, is capable of specifically detecting TOX3 in HEK293 and MCF-7 cells transfected with TOX3 vector (FIG. 5C). Vector control demonstrates that HEK 293 cells do not endogenously express TOX3, while MCF-7 express a minimal level of native TOX3 protein (FIG. 5C).

Example 6

Analysis of TOX3 Protein Expression in Breast Cancer Tumors Using Anti-TOX3 Antibodies TOX3 protein levels in breast cancer tumors can be analyzed using anti-TOX3 antibodies, such as AJ33. These studies complement gene expression studies, in order to understand the distinction between tumors that express or do not express TOX3. Indeed, protein expression profiling has also been undertaken as a method to subtype breast cancers. Analysis of tissue arrays that include normal breast tissue as well as normal tumor-adjacent breast tissue is also of particular interest to understand interactions between cell and tissue compartments in various organ structures in the mammary gland. Staining for TOX3 in breast tissue microarray using AJ33 demonstrates that normal, non-tumor samples not show TOX3 staining (FIG. 5D). By contrast, AJ33 detection of TOX3 results in dark compact intracellular positive staining in various tumor samples (FIG. 5E). Anti-TOX3 antibody, AJ33, is capable of distinguishing positive TOX3 staining in tumor cells, compared to normal breast tissue. This platform provides a means to quantify of TOX3 expression levels that may variable both in tumor cells and normal breast tissue.

Establishing the quantification of TOX3 expression, both at the gene transcript and protein level is important as initial qRT-PCR studies have shown highly variable levels of TOX3 expression across normal tissue, tumor samples, and breast cancer cell lines. For example, TOX3 gene transcript (i.e., mRNA) levels were shown to be variable even between two ostensibly normal breast tissue samples, and with even higher expression from tissue derived from breast cancer patient samples (FIGS. 4A and 4B). Thus, protein detection of TOX3 serves as a complementary approach to qRT-PCR studies to establish when upregulation of TOX3 can ultimately lead to tumorigenesis, and how expression of TOX3 in normal tissue adjacent to TOX3 high-expressing cells may interact for cancer pathogenesis.

Example 7

Figure 3:
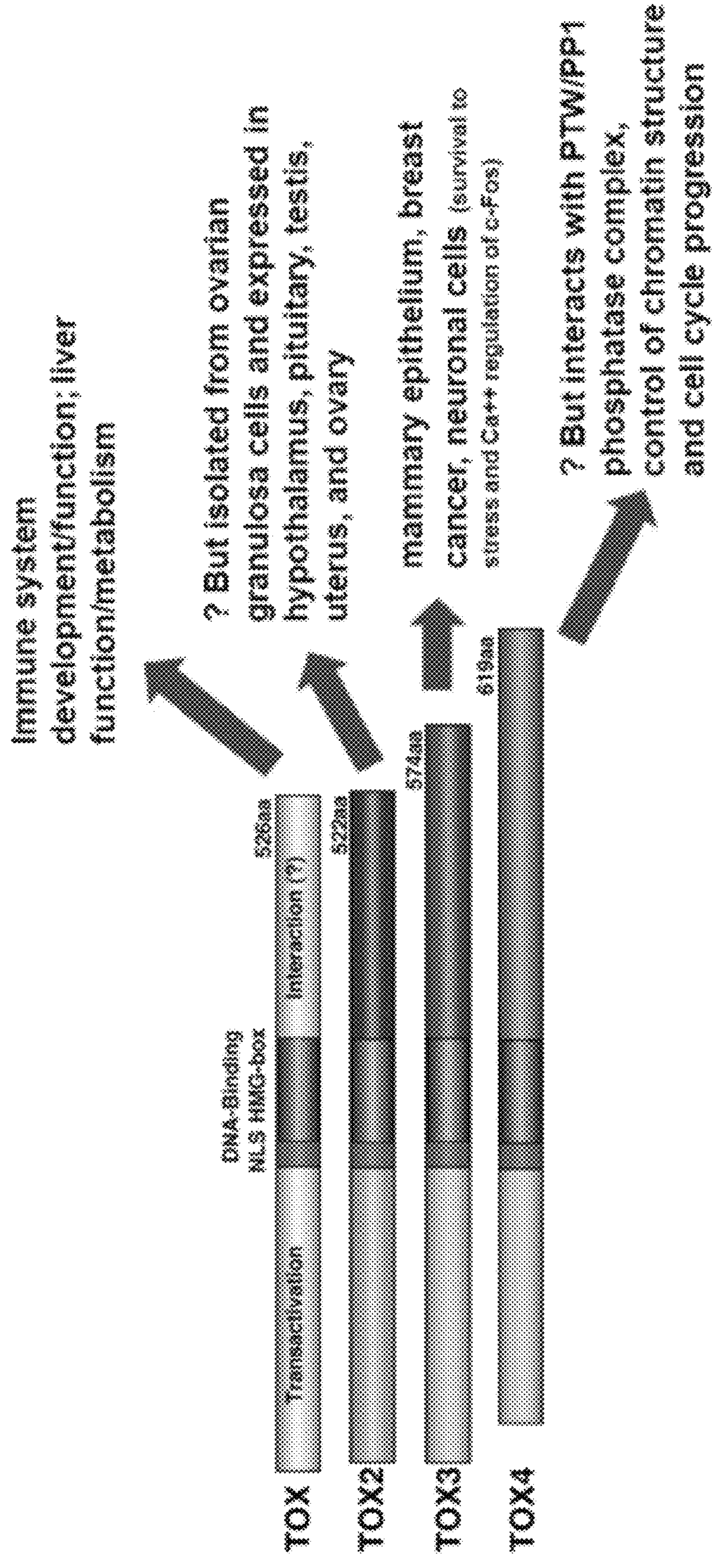
FIG. 3 depicts divergent roles of TOX family members in various tissues of the body.

Generation of a Novel In Vivo Animal Model for Expression of TOX3 in Breast Tissue Characterization of in vitro TOX3 gene and protein expression levels is complimented by in vivo studies using animal models. As such, Applicant clarified the role of TOX3 in initiating tumorigenesis by developing a novel in vivo animal model for expression of TOX3 in breast tissue. The above examples focus on a continuing role for TOX3 in tumor maintenance or progression. However, TOX3 may be an initiator of disease rather than maintenance of the tumor phenotype, as TOX itself plays a transient role during development of the immune system (FIG. 3). In this context, creation of an in vivo model system is particularly important to allow mechanistic dissection of the role of TOX3 in breast cancer, including tumor induction. Data disclosed herein suggest that overexpression rather than mutation or loss of TOX3 likely is involved in disease; thus a conditional deletion or mutation of the protein in vivo is generated.

Figure 6:
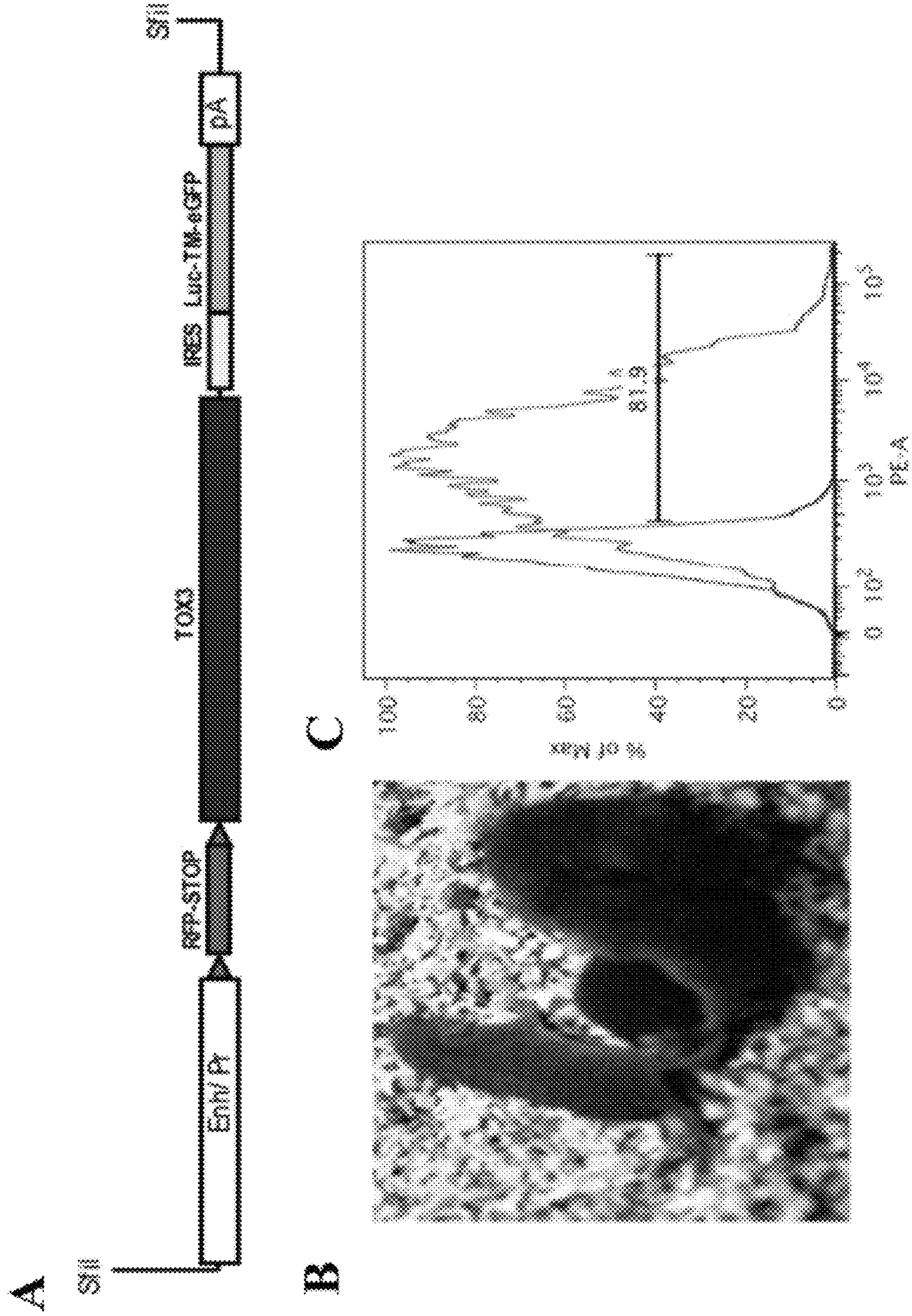
FIG. 6 TOX3 can influence mammary epithelial cell development in Cre-activated TOX3 transgenic mice. (A) TOX3 cassette was inserted into inducible Cre-$lox_p$ IRES vector designed as shown. Expression cassette of human TOX3 is flanked by SfiI restriction sites, and contains dual reporters, RFP and Luciferase-eGFP. Using Cre-mediated inducible expression of TOX3 and a GFP-luciferase fusion protein as marker, TOX3Tg mated with MMTV-cre strain established inducible expression in mammary tissue. (B) Red animal under fluorescent light demonstrate successful integration and expression of engineered cassette containing TOX3. Animals expressed RFP ubiquitously. (C) RFP expressed in mammary epithelial cells as measured using flow cytometry (FACS). (D) TOX3 expressed in mammary epithelial cells using AJ33 antibody (TG=transgenic animal with TOX3 casette, WT=cre+ non-transgenic). (E) Red fluorescence and luciferase expression is clearly visible when imaging animals under fluorescent light.
Figure 6:
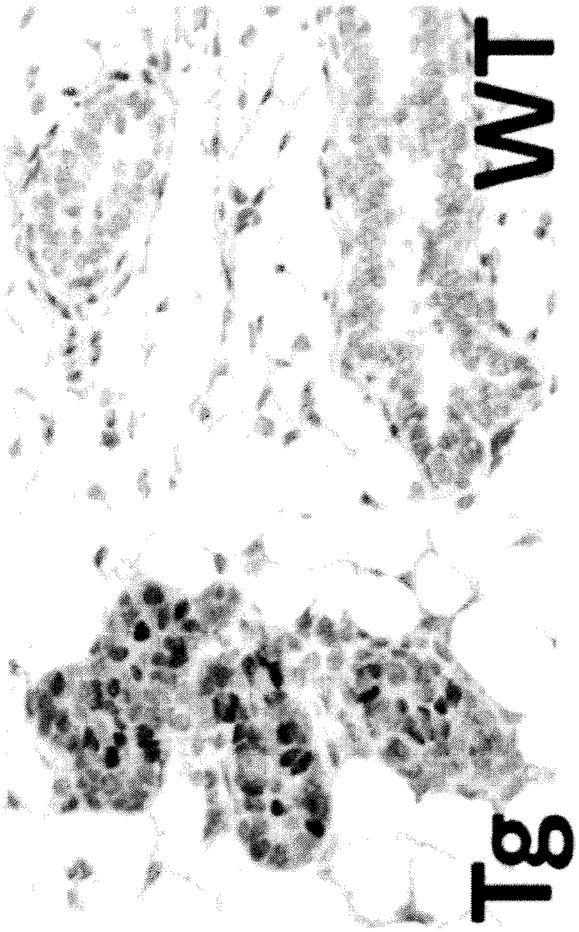
Figure 6:
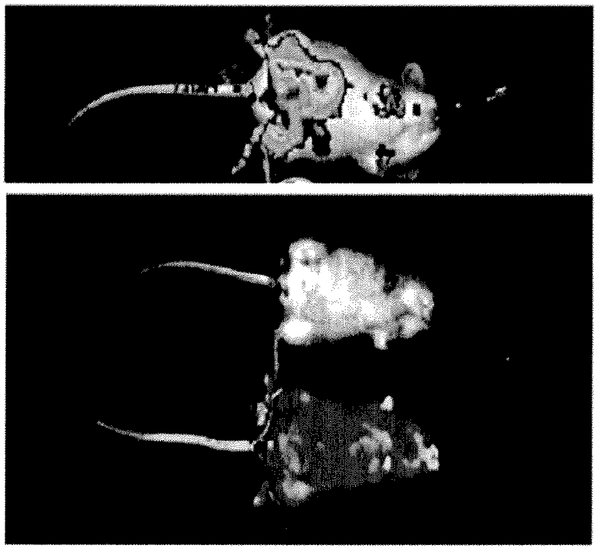

To determine whether alterations in TOX3 expression can directly induce cancerous changes in breast tissue or increase susceptibility to cancer, transgenic mice are produced that highly express this nuclear factor specifically in the breast. In addition, mice are generated with reversible transgene expression, such as with a tetracycline-inducible system, which would give finer control of timing of expression and allow experiments to distinguish a role for the protein in induction versus maintenance of tumors. To accomplish this, human TOX3 has been cloned from a highly-expressing tumor sample (FIG. 4), by high fidelity RT-PCR. For the reasons presented above (see FIG. 5B), primers are designed to clone TOX3 variant 1 for this purpose. From preliminary sequence analysis (based on independent PCR reactions) a single silent polymorphism in the coding region from this patient's tumor, when compared to the public database sequence, is found. This is consistent with Applicant's hypothesis that mutations in the coding sequence of TOX3 are not associated with breast cancer, while level of expression is. This most basic issue has not been addressed in the context of breast cancer. Cloned TOX3 cassette was inserted into inducible Cre-lox$_p$ IRES vector designed as shown (FIG. 6A). Expression cassette of human TOX3 is flanked by SfiI restriction sites, and contains dual reporters, RFP and Luciferase-eGFP.

Transgenic mice are produced using a mouse mammary tumor virus (MMTV) promoter-based expression vector obtained from Dr. Windle (Virginia Commonwealth University). The human TOX3 cDNA is inserted into exon 3 of the rabbit beta globin gene in this vector. There are no translation start sites in the globin sequences upstream of the cDNA, but there is an upstream exon/intron to allow splicing, necessary to obtain expression in transgenic mice. This vector gives high-level expression in breast tissue in vivo. Genetic background can play an important role in rodent tumor models, as it does in human disease. These transgenic mice will be produced in the FVB/N strain, an easy strain for production of transgenic mice, but most importantly, also found to be susceptible to mammary tumor formation by expression of various genes under control of the MMTV promoter, including Erbb2 (Her2/neu) (as described herein), Hras1 and Wnt1.

First generation progeny of transgenic founder mice (MMTV-huTOX3 Tg) are screened for expression of TOX3 in breast tissue by RT-PCR, and via Western blot using the antibody produced as described herein. The rabbit β-globin untranslated sequence allows specific detection of the transgene, both at the level of RNA and DNA by PCR. Strains with high level of expression are bred for additional characterization. Two types of analyses are conducted. First, spontaneous tumor formation in these mice is examined. Second, the ability of TOX3 expression to modulate oncogene-driven tumor formation as described below is analyzed. These experiments are conducted simultaneously, as the former also acts as a control for the latter.

Mammary glands from MMTV-huTOX3 Tg and wildtype littermate virgin mice are examined at 5 weeks, 2 months, and 4 months postpartum to look for structural differences, and of course tumor formation. Since, TOX3 appears to be associated with ER+ disease it is also possible that there may be effects induced by hormone responsiveness. To test this, MMTV-huTOX3 Tg and wildtype littermate mice during pregnancy are compared. The mouse mammary gland undergoes well-characterized differentiation changes during pregnancy and lactation that might affect TOX3 activity.

Figure 7:
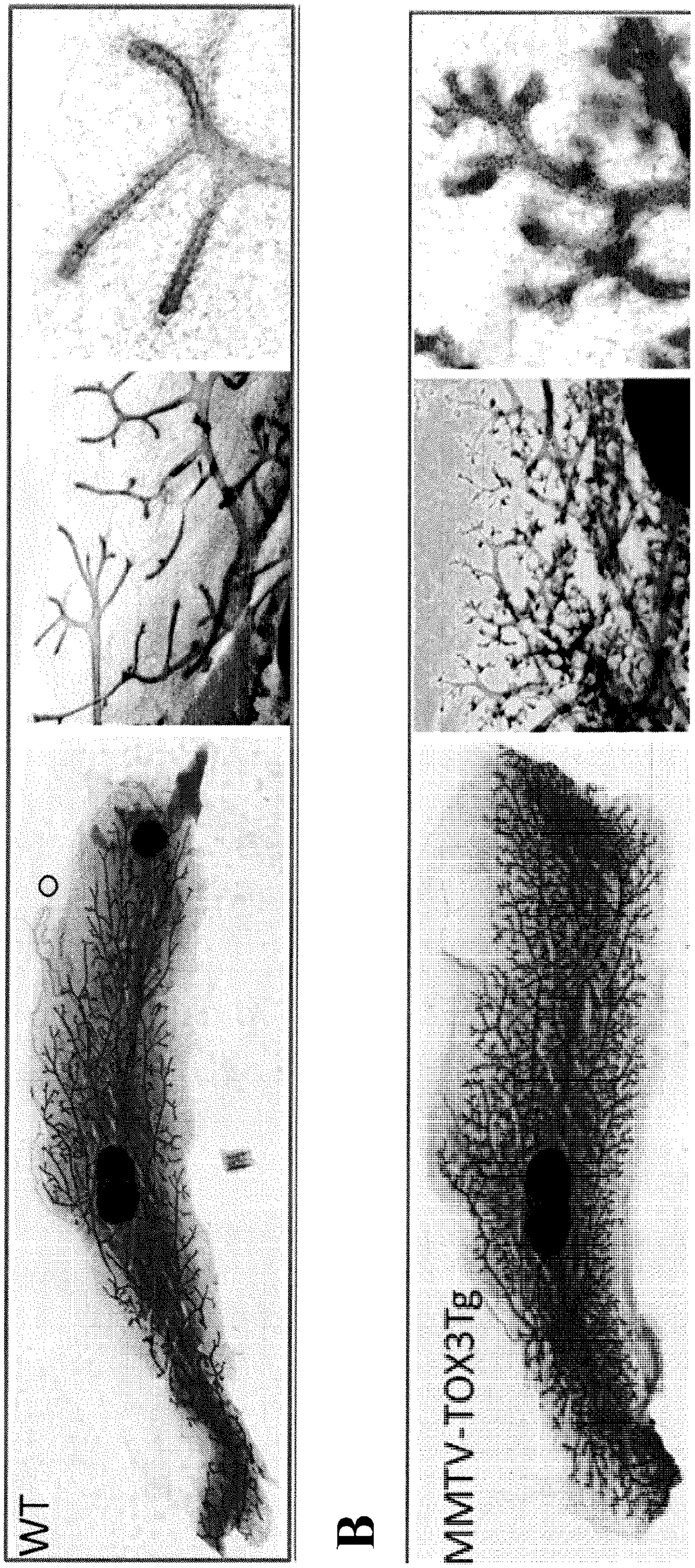
FIG. 7 Pathological changes in transgenic animal tissues. (A) Wild-type animals display normal branching in mammary tissue, various magnifications are shown. (B) By contrast, significantly enhanced branching is visible in MMTV-TOX3Tg transgenic mice, various magnifications are shown.

Further breeding of MMTV-huTOX3 Tg mated with MMTV-cre strain allows for an inducible expression system in mammary tissue. These results clearly demonstrate that TOX3 can influence mammary epithelial cell development in Cre-activated TOX3 transgenic mice. Under fluorescent light, TOX3 Tg animals display red color characteristic of RFP protein, thereby demonstrating successful integration and expression of engineered cassette containing TOX3 (FIG. 6B). The expression of reporter RFP was ubiquitous, showing successful germline integration and propagation in transgenic progeny. Further analysis using flow cytometry (FACS) show RFP to be expressed in mammary epithelial cells as measured using flow cytometry (FIG. 6C). Application of the AJ33 to tissue samples from TOX3 Tg animals demonstrate that TOX3 expressed in mammary epithelial cells specifically (FIG. 6D). Whereas RFP is ubiquitously expressed, luciferase, under the control of the TOX3-cre engineered cassette displays tissue specific localization, including in the mammary compartment under fluorescent light (FIG. 6E). These results clearly demonstrate successful achievement of TOX3 Tg mice, including application of an inducible system displaying tissue specific localization in mammary epithelium. Remarkably, enhanced branching in mammary tissues is readily apparent in MMTV-huTOX3 Tg transgenic animals compared to wild-type animals (FIG. 7). Branching cellular morphogenesis and fat pad invasion are key development and regulatory processes for formation and maintenance breast organ structures and tissue. These results establish a role for TOX3 in the formation of mammary epithelium, particularly with respect to branch formation, and provide a model for evaluating TOX3 expression and its potential impact on breast cancer pathogenesis.

The ability of TOX3 to modulate the timing, incidence, phenotype, or progression of disease induced by Erbb2 (Her2/neu) is examined. Although the Erbb2 subtype is more associated with ER-disease, preliminary data has indicted that there can be overlap in expression of Erbb2 and TOX3 in breast cancer tumors (FIG. 1). There are two relevant transgenic mouse models, both on a FVB/N background, and both commercially available that express Erbb2 under the MMTV promoter and lead to disease. In one, expression of unactivated rat Erbb2 in mice leads to focal mammary tumors that first appear at 4 months. Guy C T, et al., Expression of the neu-protooncogene in the mammary epithelium of transgenic mice induces metastatic disease. *Proc Natl Acad Sci USA.* 1992; 89(22):10578-82. There is also a high frequency of secondary metastatic disease in the lung. In the other model, expression of a transforming mutated version of rat Erbb2 results in in multifocal disease involving the whole epithelium. Muller W J, et al., Single-step induction of mammary adenocarcinoma in transgenic mice bearing the activated c-neu oncogene. *Cell.* 1988; 54(1):105-15.

These mice are utilized to determine the level of up regulation of endogenous TOX3 in Erbb2-induced tumors. This foundational experiment is of great interest, particularly because the comparison between the incidence of expression of TOX3 in focal and the incidence of expression of TOX3 to multi-focal disease. In addition, these Tg lines are bred to MMTV-huTOX3 Tg produced as described herein, to determine if disease induction or progression is affected. Given the relatively long lag time for disease induction in Erbb2 Tg mice, TOX3 expression supplies a "second hit" to promote disease, it is reasonable to expect that this is detectable by a significant shift in kinetics. Other differences in disease due to expression of TOX3 may be detected.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the forms of TOX proteins, including TOX3 variants, method of detecting TOX proteins, sources of TOX protein or gene transcript expression, binding activities for TOX proteins and the techniques used to manufature or express TOX proteins, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed:

1. An isolated monoclonal antibody that binds to the TOX3 polypeptide set forth in SEQ ID NO: 7.

2. The isolated antibody of claim 1, wherein the isolated antibody preferentially binds cells obtained from tumor tissue.

3. A pharmaceutical composition, comprising: an amount of an isolated TOX3 monoclonal antibody that binds to the TOX3 polypeptide set forth in SEQ ID NO: 7; and a pharmaceutically acceptable carrier.

4. The isolated antibody of claim 1, wherein the isolated antibody is a rabbit monoclonal antibody.

* * * * *